(12) United States Patent
 Amanatullah

(10) Patent No.: US 10,806,518 B2
(45) Date of Patent: Oct. 20, 2020

(54) METHODS FOR AUGMENTING A SURGICAL FIELD WITH VIRTUAL GUIDANCE AND TRACKING AND ADAPTING TO DEVIATION FROM A SURGICAL PLAN

(71) Applicant: Arthrology Consulting, LLC, Palo Alto, CA (US)

(72) Inventor: Derek Amanatullah, Palo Alto, CA (US)

(73) Assignee: Arthrology Consulting, LLC, Palo Alto, CA (US)

(*) Notice: Subject to any disclaimer, the term of this patent is extended or adjusted under 35 U.S.C. 154(b) by 21 days.

(21) Appl. No.: 16/238,504

(22) Filed: Jan. 2, 2019

(65) Prior Publication Data
US 2019/0231433 A1    Aug. 1, 2019

Related U.S. Application Data

(63) Continuation-in-part of application No. 15/594,623, filed on May 14, 2017, now abandoned, and a continuation-in-part of application No. 15/499,046, filed on Apr. 27, 2017, now Pat. No. 10,194,990.

(60) Provisional application No. 62/612,895, filed on Jan. 2, 2018, provisional application No. 62/612,901, filed on Jan. 2, 2018, provisional application No.
(Continued)

(51) Int. Cl.
| A61B 34/10 | (2016.01) |
| A61B 5/00 | (2006.01) |
| A61B 90/00 | (2016.01) |
| A61B 17/17 | (2006.01) |

(Continued)

(52) U.S. Cl.
CPC ............ *A61B 34/10* (2016.02); *A61B 5/0037* (2013.01); *A61B 5/0064* (2013.01); *A61B 5/4528* (2013.01); *A61B 5/7425* (2013.01); *A61B 17/1703* (2013.01); *A61B 17/175* (2013.01); *A61B 17/1764* (2013.01); *A61B 90/37* (2016.02); *G09B 23/28* (2013.01); *A61B 17/155* (2013.01); *A61B 17/157* (2013.01);
(Continued)

(58) Field of Classification Search
CPC .. G06T 19/00; G06T 19/006; A61B 34/00–77
See application file for complete search history.

(56) References Cited

U.S. PATENT DOCUMENTS

| 2014/0303990 A1* | 10/2014 | Schoenefeld | G06F 19/321 705/2 |
| 2017/0258526 A1* | 9/2017 | Lang | A61F 2/389 |
| 2018/0289387 A1* | 10/2018 | Khajavi | A61B 50/3001 |

* cited by examiner

*Primary Examiner* — Ryan McCulley
(74) *Attorney, Agent, or Firm* — Run8 Patent Group, LLC; Peter Miller

(57) ABSTRACT

One variation of a method includes: accessing a virtual patient model defining a target resected contour of a hard tissue of interest; after resection of the hard tissue of interest during a surgical operation, accessing an optical scan recorded by an optical sensor facing a surgical field occupied by a patient, detecting a set of features representing the patient in the optical scan, registering the virtual patient model to the hard tissue of interest in the surgical field based on the set of features, and detecting an actual resected contour of the hard tissue of interest in the optical scan; and calculating a spatial difference between the actual resected contour of the hard tissue of interest and the target resected contour of the hard tissue of interest represented in the virtual patient model registered to the hard tissue of interest in the surgical field.

20 Claims, 6 Drawing Sheets

Related U.S. Application Data

62/363,022, filed on Jul. 15, 2016, provisional application No. 62/328,330, filed on Apr. 27, 2016.

(51) Int. Cl.
*G09B 23/28* (2006.01)
*A61B 17/15* (2006.01)

(52) U.S. Cl.
CPC ... *A61B 2034/102* (2016.02); *A61B 2034/104* (2016.02); *A61B 2034/105* (2016.02)

METHODS FOR AUGMENTING A SURGICAL FIELD WITH VIRTUAL GUIDANCE AND TRACKING AND ADAPTING TO DEVIATION FROM A SURGICAL PLAN

CROSS-REFERENCE TO RELATED APPLICATIONS

This application is a continuation-in-part application of U.S. patent application Ser. No. 15/594,623, filed on 14 May 2017, which claims the benefit of U.S. Provisional Application No. 62/363,022, filed on 15 Jul. 2016, and which is a continuation-in-part application of U.S. patent application Ser. No. 15/499,046, filed on 27 Apr. 2017, which claims the benefit of U.S. Provisional Application No. 62/328,330, filed on 27 Apr. 2016, and U.S. Provisional Application No. 62/363,022, filed on 15 Jul. 2016, all of which are incorporated in their entireties by this reference.

Furthermore, this Application claims the benefit of U.S. Provisional Application No. 62/612,895, filed on 2 Jan. 2018, and U.S. Provisional Application No. 62/612,901, filed on 2 Jan. 2018, both of which are incorporated in their entireties by this reference.

TECHNICAL FIELD

This invention relates generally to the field of augmented reality and more specifically to a new and useful method for registering features of a patient's body within a surgical field to provide virtual guidance in the field of augmented reality.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1A:
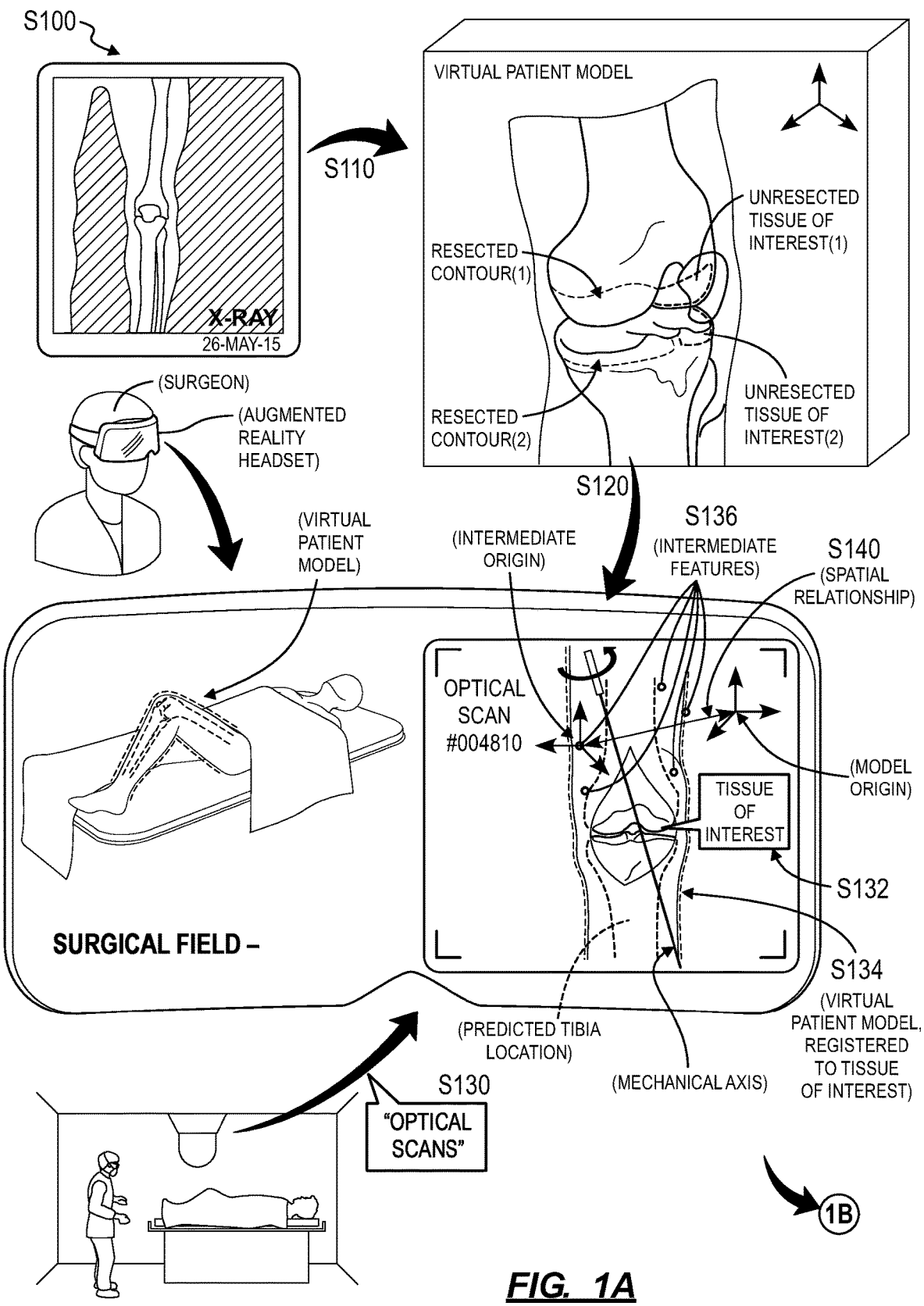
FIGS. 1A and 1B are flowchart representations of a method.
Figure 1B:
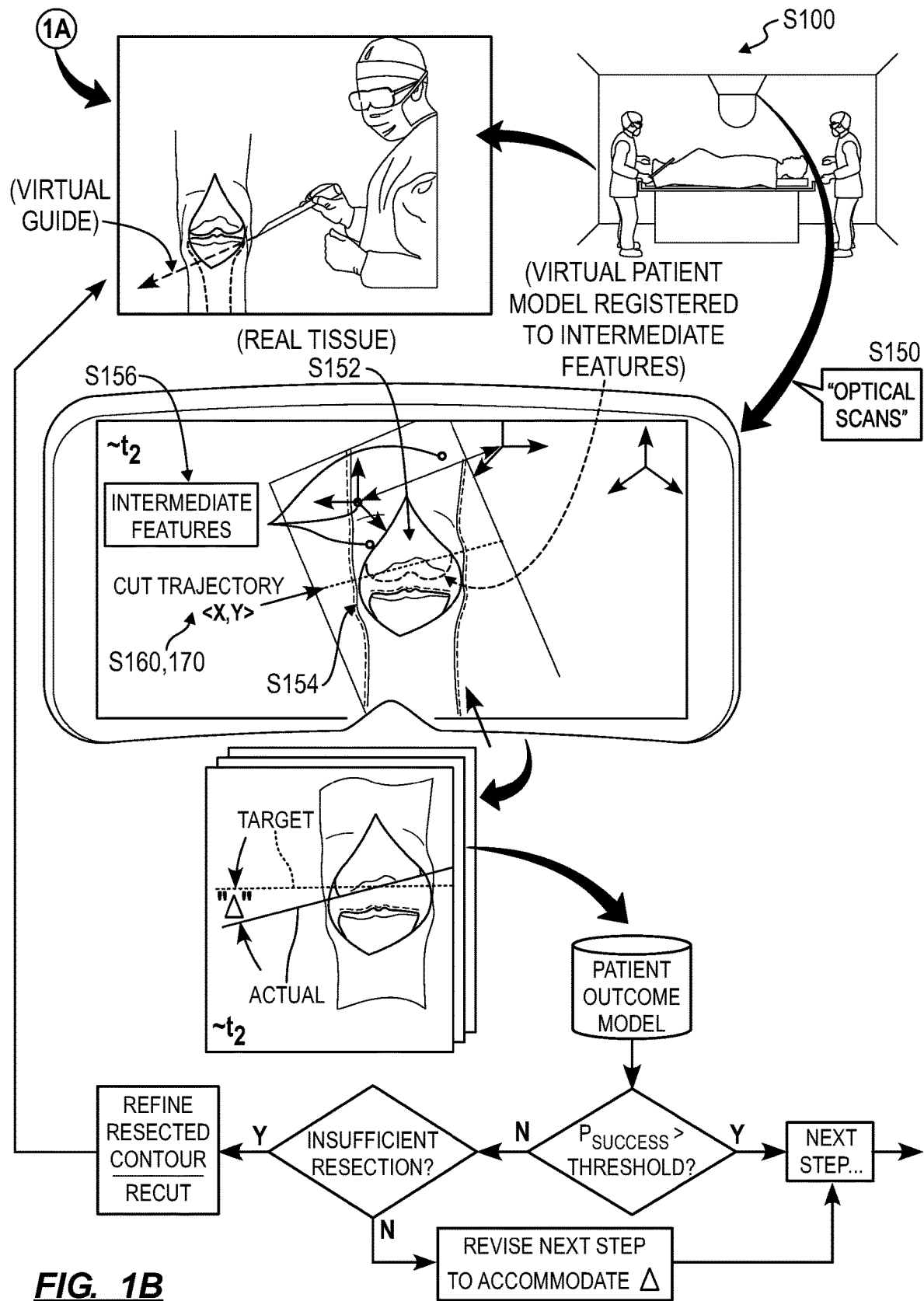

As shown in FIGS. 1A and 1B, a method S100 for registering features of a patient in a surgical field includes accessing a virtual patient model representing a hard tissue of interest of the patient in Block S120, the virtual patient model generated from a pre-operative scan of the hard tissue of interest of the patient. The method S100 also includes, during a first period of time succeeding incision of the patient proximal the hard tissue of interest and prior to resection of the hard tissue of interest within a surgical operation: accessing a first sequence of optical scans recorded by an optical sensor facing a surgical field occupied by the patient in Block S130; detecting a first contour of the hard tissue of interest in the first sequence of optical scans in Block S132; registering virtual hard tissue features defined in the virtual patient model to the first contour of the hard tissue of interest in Block S134; and detecting a set of intermediate features, on the patient and proximal the hard tissue of interest, in the first sequence of optical scans in Block S136. The method S100 further includes deriving a spatial relationship between the set of intermediate features and the virtual patient model based on registration of the virtual patient model to the hard tissue of interest in Block S140. The method S100 also includes, during a second period of time succeeding resection of the hard tissue of interest within the surgical operation: accessing a second sequence of optical scans recorded by the optical sensor in Block S150; detecting the set of intermediate features in the second sequence of optical scans in Block S156; registering the virtual patient model to the hard tissue of interest based on the spatial relationship and the set of intermediate features detected in the second sequence of optical scans in Block S154; and detecting a second contour of the hard tissue of interest in the second sequence of optical scans in Block S152. The method S100 further includes detecting a spatial difference between virtual hard tissue features defined in the virtual patient model and the second contour of the hard tissue of interest detected in the second sequence of optical scans in Block S160.

One variation of the method S100 includes accessing a virtual anatomical model representing a hard tissue of interest in human anatomy in Block S120. This variation of the method S100 also includes, during a first period of time succeeding incision of the patient proximal the hard tissue of interest and prior to resection of the hard tissue of interest within a surgical operation: accessing a first sequence of optical scans recorded by an optical sensor facing the surgical field occupied by the patient in Block S130; detecting a first contour of the hard tissue of interest in the first sequence of optical scans in Block S132; registering virtual hard tissue features defined in the virtual anatomical model to the first contour of the hard tissue of interest in Block S134; and detecting a set of intermediate features, on the patient and proximal the hard tissue of interest, in the first sequence of optical scans in Block S136. This variation of the method S100 further includes deriving a spatial relationship between the set of intermediate features and the virtual anatomical model based on registration of the virtual anatomical model to the hard tissue of interest in Block S140. This variation of the method S100 also includes, during a second period of time succeeding resection of the hard tissue of interest within the surgical operation: accessing a second sequence of optical scans recorded by the optical sensor in Block S150; detecting a second contour of the hard tissue of interest in the second sequence of optical scans in Block S152; detecting the set of intermediate features in the second sequence of optical scans in Block S156; and, in response to presence of the second contour in place of the first contour in the second sequence of optical scans, registering the virtual anatomical model to the hard tissue of interest based on the spatial relationship and the set of intermediate features detected in the second sequence of optical scans in Block S154. Finally, this variation of the method S100 also includes detecting a spatial difference between virtual hard tissue features defined in the virtual anatomical model and the second contour of the hard tissue of interest detected in the second sequence of optical scans in Block S160.

Figure 3:
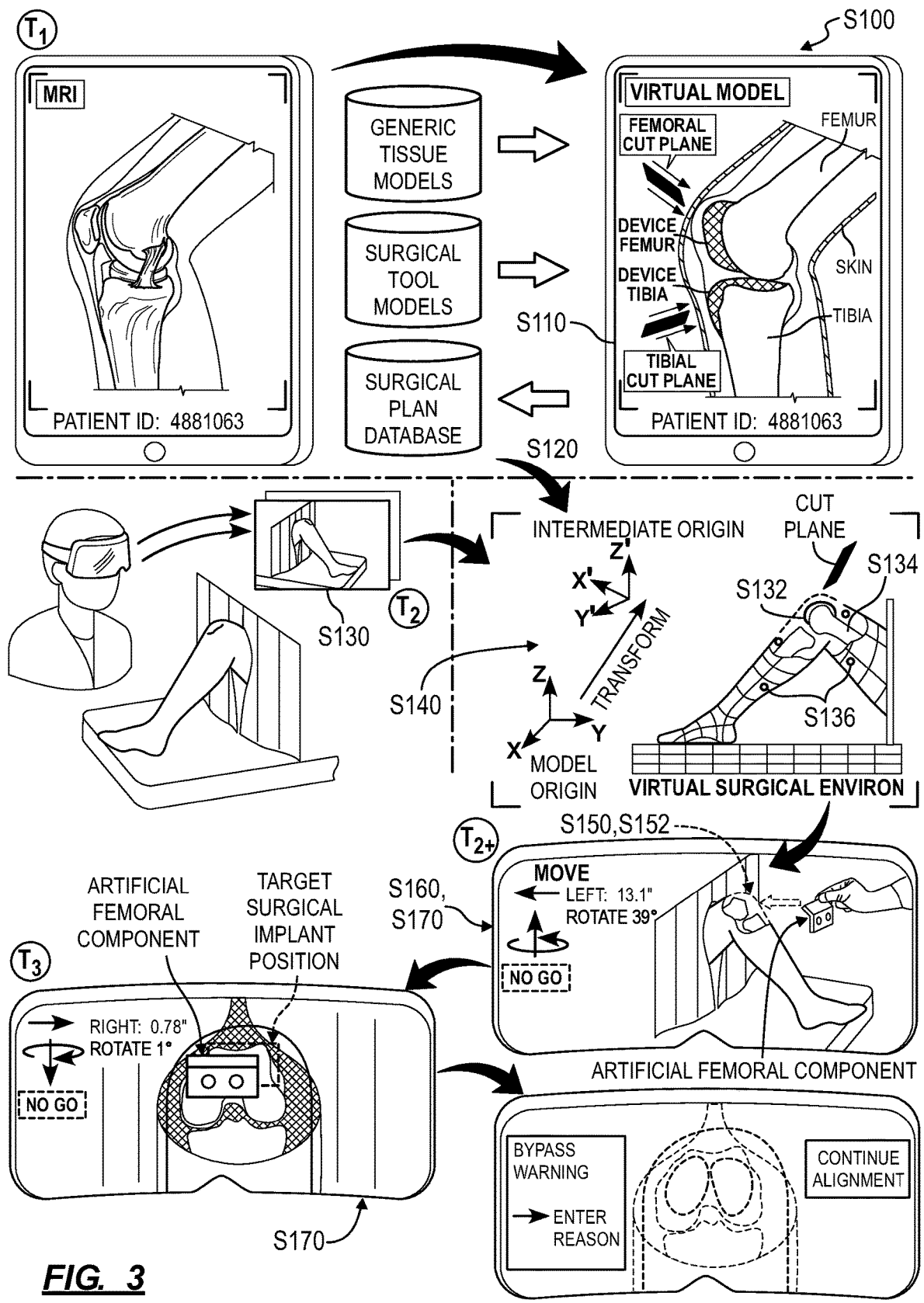
FIG. 3 is a flowchart representation of one variation of the method.

Another variation of the method S100 shown in FIG. 3 includes accessing a virtual patient model defining a target resected contour of a hard tissue of interest in Block S120. This variation of the method S100 also includes, during a first period of time succeeding resection of the hard tissue of interest within a surgical operation: accessing a first sequence of optical scans recorded by an optical sensor facing a surgical field occupied by a patient in Block S150; detecting a set of features representing the patient in the first sequence of optical scans in Block S156; registering the virtual patient model to the hard tissue of interest in the surgical field based on the set of features in Block S154; and detecting an actual resected contour of the hard tissue of interest in the first sequence of optical scans in Block S152. This variation of the method S100 further includes: calculating a spatial difference between the actual resected contour of the hard tissue of interest detected in the first sequence of optical scans and the target resected contour of the hard tissue of interest represented in the virtual patient model registered to the hard tissue of interest in the surgical field in Block S160; and presenting the spatial difference to a surgeon during the surgical operation in Block S170.

Yet another variation of the method S100 includes accessing a virtual patient model defining a target position of a artificial implant on a hard tissue of interest in Block S120. This variation of the method S100 also includes, during a first period of time succeeding placement of the artificial implant on the hard tissue of interest within a surgical operation: accessing a first sequence of optical scans recorded by an optical sensor facing a surgical field occupied by a patient in Block S150; detecting a set of features representing the patient in the first sequence of optical scans in Block S156; registering the virtual patient model to the hard tissue of interest in the surgical field based on the set of features in Block S154; and detecting an actual position of the artificial implant on the hard tissue of interest in the first sequence of optical scans in Block S152. This variation of the method S100 further includes: calculating a spatial difference between the actual position of the artificial implant on the hard tissue of interest detected in the first sequence of optical scans and the target position of the artificial implant on the hard tissue of interest represented in the virtual patient model registered to the hard tissue of interest in the surgical field in Block S160; and presenting the spatial difference to a surgeon during the surgical operation in Block S170.

2. Applications: Registration

As shown in FIGS. 1A and 1B, a computer system can execute Blocks of the method S100 to access and transform scan data of a hard tissue of interest (e.g., bone) of a patient into a virtual patient model representing the hard tissue of interest prior to a surgical operation on the patient. For example, the computer system can generate a virtual patient model depicting the patient's left femur and left tibia prior to a left knee replacement. Later, during the surgical operation, the computer system can access optical scan data from an optical sensor (e.g., a LIDAR or other depth sensor, color camera, stereoscopic camera, thermographic camera, multispectral camera) arranged in the surgical field and sequentially narrow objects detected in these optical scan data down to the patient's hard tissue of interest, including: first identifying the patient generally (e.g., by detecting the patient's head, feet, and front or back side); identifying a region of the patient predicted to contain the hard tissue of interest; and coarsely registering the virtual patient model to this region of the patient. As the surgeon incises the patient near the hard tissue of interest, the computer system can verify that red pixels depicting blood and/or muscle tissue in the next optical scan align with the region of the patient predicted to contain the hard tissue of interest. As the surgeon displaces soft tissue to reveal the hard tissue of interest, the computer system can: detect light-colored (e.g., approximately white) pixels depicting bone in the next optical scan; extract three-dimensional ("3D") anatomical features representing this bone surface, which represented unique hard tissue anatomy of the patient; and align (or "snap") the virtual representation of the corresponding bone in the virtual patient model to these 3D anatomical features, thereby aligning the virtual patient model to the hard tissue of interest detected in the surgical field.

Furthermore, if the computer system detects a difference between the virtual patient model and the 3D features of the hard tissue of interest detected in the surgical field, the computer system can also modify the virtual patient model to better resemble these 3D features of the hard tissue of interest. The computer system can therefore detect and handle these 3D features of the hard tissue of interest as an initial "ground truth" of the patient.

However, because this hard tissue of interest may change as the surgeon resects portions of the hard tissue of interest and/or installs artificial components on or near the hard tissue of interest, these 3D features of the patient's hard tissue of interest may be removed or obscured from the optical sensor. Therefore, once the computer system has aligned the virtual patient model to the hard tissue of interest, the computer system can also define a constellation of intermediate features—remote from the hard tissue of interest—that bridge registration of the virtual patient model and the hard tissue of interest.

For example, for a left knee replacement, the computer system can: define a constellation of intermediate features for the patient's left femur that includes a mechanical axis of the patient's left femur, a global 3D skin surface profile of the patient's left upper leg, and a set of freckles, moles, or other superficial skin features on the patient's left upper leg; and define a constellation of intermediate features for the patient's left tibia that includes a mechanical axis of the patient's left tibia, a global 3D skin surface profile of the patient's left lower leg, and a set of freckles, moles, or other superficial skin features on the patient's left lower leg. Thus, as the patient's left femoral condyles and left tibial plateau are resected during the knee replacement surgery, the computer system can: continue to access optical scan data recorded by the optical sensor; track the patient, the patient's left leg, and bone surfaces in the patient's left knee in the surgical field based on features extracted from this optical scan data; align the virtual patient model of the patient's left femur and left tibia to corresponding bone features detected in the surgical field while these bone features are present and not obscured; and transition to aligning the virtual patient model of the patient's left femur and left tibia to corresponding constellations of intermediate features detected in the surgical field once the corresponding bone features are resected or are otherwise obscured from the optical sensor.

Therefore, once the patient's hard tissue of interest has been modified (e.g., resected or modified via installation of an artificial component), the computer system can transition to: handling the virtual patient model as "ground truth" for the patient; and registering the virtual patient model to the patient based on the constellation of intermediate features. In particular, once the surgeon resects the hard tissue of interest, the computer system can implement the virtual patient model as the virtual "ground truth" representation of the patient's anatomy—registered to other hard and/or soft tissue features—for all subsequent steps of the surgery such that this ground truth representation of the patient defines a preoperative anatomical state the patient regardless of changes made to the patient's anatomy during the surgery, thereby enabling the surgeon: to "look back" to quantify actual changes in the patient's anatomy during the surgery; and to "look forward" to planned future changes to the patient's anatomy during the surgery based on this virtual ground truth representation of the patient's anatomy.

The computer system can also: generate augmented reality frames representing the virtual patient model aligned with the patient's anatomy; serve these augmented reality frames to a display (e.g., a heads-up or eyes-up augmented reality display worn by a surgeon during the operation) in real-time in order to preserve a visual representation of the pre-operative state of the hard tissue of interest—as represented in the virtual patient model—for the surgeon as the surgeon modifies the hard tissue of interest throughout the surgical operation. The surgeon may therefore reference these augmented reality frames—overlaid on the patient's hard tissue of interest—to quickly visualize real changes to the hard tissue of interest from its pre-operative state.

Therefore, the computer system can execute Blocks of the method S100 throughout a real surgical operation in order to preserve an accurate representation of the original, unmodified hard tissue of interest—aligned to corresponding real features on the patient's body, even as some of these real features change. The computer system can then characterize differences between this virtual patient model and the patient's hard tissue of interest—detected in later scan data recorded by the optical sensor—as the hard tissue of interest is modified throughout the surgical operation and thus return quantitative guidance to the surgeon regarding position, orientation, and magnitude, etc. of absolute changes to the hard tissue of interest. The computer system can also: detect differences between these absolute changes to (e.g., resection of) the hard tissue of interest and target changes to the hard tissue of interest defined in a surgical plan registered to the virtual patient model; and return quantitative metrics regarding differences between these actual and target changes, thereby enabling the surgeon to confirm intent of such differences or further modify the hard tissue of interest to achieve better alignment with the surgical plan. Additionally or alternatively, the computer system can: detect differences between the absolute position of a surgical implant installed on the hard tissue of interest and a target position of the surgical implant defined in the surgical plan registered to the virtual patient model; and return quantitative metrics regarding differences between these actual and target surgical outcomes, thereby enabling the surgeon to confirm intent of such differences or modify the position of the surgical implant to achieve better alignment with the surgical plan.

Blocks of the method S100 are described herein in the context of a knee replacement surgery. However, Blocks of the method S100 can be executed by a computer system to register a virtual patient model to a patient's hard and/or soft tissue features and to preserve this virtual patient model—registered to the patient's real tissue—as a virtual ground truth state of the patient's original hard tissue of interest in any other surgical or medical application, such as: a hip replacement operation; a rotator cuff repair surgery; a heart valve replacement operation; a carpal tunnel release surgery; a cataract removal procedure; or a surgical repair of a comminuted or open fracture; etc. Furthermore, Blocks of the method S100 are described herein in the context of registering a virtual model of a hard tissue of interest to hard and soft tissue features detected in the surgical field. However, similar methods and techniques can be executed by the computer system to register a soft tissue of interest (e.g., an aortic valve, an artery, a pancreas) to other hard and/or soft features within a patient's body.

The method is also described below as executed by the computer system to generate augmented reality frames for presentation to a local surgeon in real-time during the surgery—such as through an augmented reality headset worn by the local surgeon or other display located in the operating room—to provide real-time look-back and look-forward guidance to the local surgeon. However, the computer system can implement similar methods and techniques to generate virtual reality frames depicting both real patient tissue and virtual content (e.g., target resected contours of tissues of interest defined in a virtual patient model thus registered to the real patient tissue) and to serve these virtual reality frames to a remote surgeon (or remote student). For example, the computer system can generate and serve such virtual reality frames to a virtual reality headset worn by a remote surgeon in real-time during the surgery in order to enable the remote surgeon to: monitor the surgery; manually adjust parameters of the surgery or surgical plan; selectively authorize next steps of the surgical plan; and/or serve real-time guidance to the local surgeon.

3. Applications: Deviations from Surgical Plan

Figure 2:
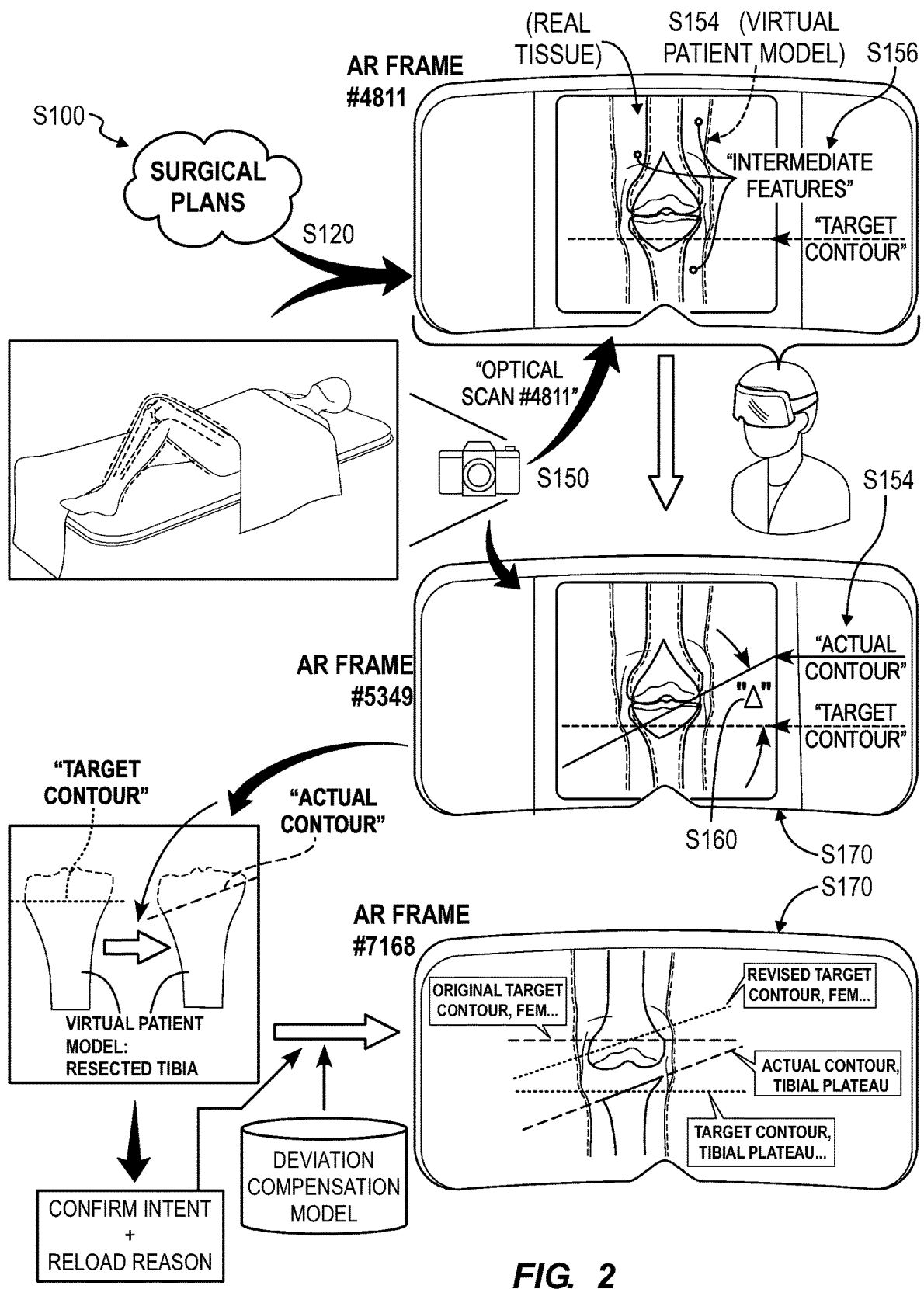
FIG. 2 is a flowchart representation of one variation of the method.

Furthermore, the computer system can execute Blocks of the method S100 to track compliance with and/or deviations from a surgical plan prescribed for the patient by a surgeon, such as prior to a surgery or in real-time during the surgery, as shown in FIGS. 2 and 3. In particular, by preserving registration of the virtual patient model—such as including virtual representations of an unresected hard tissue of interest of the patient, a target resected contour of the patient, and/or a target position of a surgical implant—to the patient's hard tissue of interest and tracking the hard tissue of interest throughout the surgery, the computer system can detect differences between actual and target resected contours of the hard tissue of interest and differences between actual and target positions of a surgical implant on or near the hard tissue of interest during the surgery. The computer system can return these differences to the surgeon in real-time—such as through augmented reality frames rendered on an augmented reality headset worn by the surgeon—in order to guide the surgeon in correcting the actual resected contour of the hard tissue of interest or adjusting a position of the surgical implant on the hard tissue of interest before moving to a next step of the surgical operation. The computer system can also adapt subsequent steps of the surgical plan to account for prior deviations from the surgical plan, such as to minimize cumulative deviation that may negatively affect the patient's surgical outcome. For example, the computer system can generate a sequence of augmented reality ("AR") frames aligned to the hard tissue of interest in the surgeon's field of view and serve these augmented reality frames to an AR headset or AR glasses (or to another display in the surgical field) in order to visually indicate to the surgeon compliance with and/or deviation from steps of the surgical plan.

In particular, the computer system can access a surgical plan—such as defined by the computer or entered manually by a surgeon, radiologist, engineer, technician, etc. before or during the surgery—defining a sequence of target resected contours (or "resected contours") of a patient's hard tissue of interest resulting from a sequence of surgical steps performed on the hard tissue of interest during an upcoming surgery. During the subsequent surgery, the computer system can: access optical scan data from an optical sensor arranged near the surgical field; implement computer vision techniques to detect a hard tissue of interest (or other tissues surrounding the hard tissue of interest) in the surgical field; and virtually align a virtual representation of the unresected hard tissue of interest with the hard tissue of interest detected in the surgical field. Throughout the surgery, the computer system can: continue to capture and/or access optical scan data of the surgical field via the optical sensor (e.g., at a rate of 24 frames-per-second); and extract actual contours of the hard tissue of interest in these optical scan data as the surgeon incises soft tissue near the hard tissue of interest, resects the hard tissue of interest, and eventually locates a surgical implant on the hard tissue of interest. In response to differences between the actual resected contour of the hard tissue of interest detected in these optical scan data and the target resected contour—represented in the *virtual patient model* and/or defined by the surgical plan—the computer system can either: prompt the surgeon to refine the actual resected contour to achieve grater alignment with the target resected contour if the actual resected contour extends beyond the target resected contour; or update subsequent steps of the surgical plan to compensate for excessive removal of material from the hard tissue of interest if the target resected contour extends beyond the actual resected contour. Alternatively, if the surgeon confirms the actual resected contour of the hard tissue of interest, the computer system can update subsequent steps of the surgical plan to compensate for this deviation from the original surgical plan. Therefore, computer system can execute Blocks of the method S100 to detect intended and unintended deviations from an original surgical plan and then modify the original surgical plan to compensate for these deviations and thus limit cumulative deviation from the original surgical plan upon completion of the surgery.

For example, the computer system can determine—based on a difference between a virtual patient model and a hard tissue of interest detected in optical scan data of a surgical field—that a surgeon (unintentionally or unknowingly) resected a tibial plateau two degrees offset from a planned cut to the tibial plateau as defined in a surgical plan. The computer system can then prompt or guide the surgeon to recut the tibial plateau in order to reduce this offset. Alternatively, if the surgeon confirms the offset from the surgical plan, the computer system can instead modify the surgical plan automatically to adjust a target contour of the adjacent femoral head of the patient by two degrees in the opposite direction in order to compensate for deviation from the surgical plan at the tibial plateau. Yet alternatively, the computer system can modify the surgical plan to offset the trajectory of a bore into the adjacent femur—to accept an artificial femoral component—by two degrees from normal to the actual resected contour to the tibial plateau such that the artificial femoral component properly mates with an artificial tibial component installed on the offset resected contour of the tibial plateau. In particular, the computer system can adapt the surgical plan to counteract this deviation at the tibial plateau. Yet alternatively, the computer system can: determine that this difference between the actual and target resected contours of the tibial plateau prescribed in the surgical plan falls within an acceptable tolerance range defined for this step of the surgery; record this deviation within a log file for the surgical operation; and repeat this process for other steps of the surgery.

The computer system can also automatically modify a surgical plan to correct or accommodate for intentional deviations from the surgical plan performed by the surgeon, thereby empowering the surgeon to adapt the surgical plan inter-operatively. For example, the computer system can receive a command from the surgeon to rotate a target resected contour to the tibial plateau of the patient—as defined in the original surgical plan—by one degree and to move the target resected contour five millimeters distally, such as after the surgeon has opened the patient's knee and inspected the patient's tibia and femur bone structures. The computer system can then modify the surgical plan accordingly, such as by modifying the target resected contour of the patient's femoral condyle defined in the surgical plan to preserve parallelism to and coaxiality with the tibial plateau. Therefore, the computer system can enable a surgeon to manually adjust a current stop of the surgical plan inter-operatively and then automatically adapt remaining steps of the surgical plan to achieve an acceptable patient outcome accordingly.

Based on historical deviations from a particular surgical plan during one surgery and/or across multiple surgeries by a particular surgeon, the computer system can predict deviations in future surgeries and preemptively adapt surgical plans for those future surgeries to compensate for these predicted future deviations. For example, based on historical surgical data, the computer system can determine that a particular surgeon typically cuts the tibial plateau within a tolerance of five degrees of a target resected contour as defined in the surgeon's surgical plans for a knee replacement surgery. The computer system can also determine that most actual resected contours to tibial plateaus fall between three degrees and five degrees offset from the target resected contour for this surgeon. The computer system can then predict that future cuts to tibial plateaus performed by this surgeon are likely to fall within three degrees and five degrees from the target resected contour defined in the surgeon's future surgical plans. The computer system can then preemptively calculate a tolerance stackup for the surgeon's knee replacement surgeries resulting from, for example, consistent five degree deviations in tibial plateau incisions and then adapt surgical plans for future knee replacement surgeries to allow a deviation tolerance band of five degrees for tibial plateau incisions based on the tolerance stackup. Alternatively, the computer system can generate additional virtual guides or cut planes for the surgeon to improve the surgeon's cut tolerance and similarly present augmented reality frames depicting these virtual guides or cut planes to the surgeon.

In another example, the computer system can extract data indicating that several surgeons typically bore into the femur three degrees offset from a prescribed femoral bore incision in a particular surgical plan. The computer system can adjust a particular surgical plan defined by one of these surgeons to offset the femoral bore incision by three degrees opposite typical off-axis boring performed by the several surgeons. Therefore, the computer system can preemptively adjust surgical plans according to historical surgical data to preempt deviations, accommodate or preemptively adapt to frequent deviations, and/or improve surgical plans to reflect a consensus of surgeon preferences.

Furthermore, based on historical deviations from a particular surgical plan during one surgery, across multiple surgeries of the same type by a particular surgeon, or across a population of patients undergoing a particular surgery type, the computer system can isolate the surgical plan and/or surgical plan deviations predicted to yield positive (and negative) outcomes for patients and guide surgeons in defining future surgical plans accordingly.

4. System

Blocks of the method S100 can be executed locally in an operating room and/or remotely, such as: by a local computing device within an operating room or within a hospital; by a remote computing device (e.g., a remote server); and/or by a distributed computer network. Blocks of the method S100 can also be executed locally and/or remotely by a cluster of computers. Blocks of the method S100 can additionally or alternatively be executed by an augmented reality headset, augmented reality glasses, or other augmented reality device, such as worn by a surgeon in the operating room. A computing device executing Blocks of the method S100 can also interface with: an augmented reality device; one or more 2D color cameras, 3D cameras, and/or depth sensors (e.g., a LIDAR sensors, a structured light sensor); sensor-enabled surgical tools; and/or other sensors and actuators within the operating room.

However, any other local, remote, or distributed computer system—hereinafter referred to as "the computer system"—can execute Blocks of the method S100 substantially in real-time.

5. Virtual Patient Model

Figure 4:
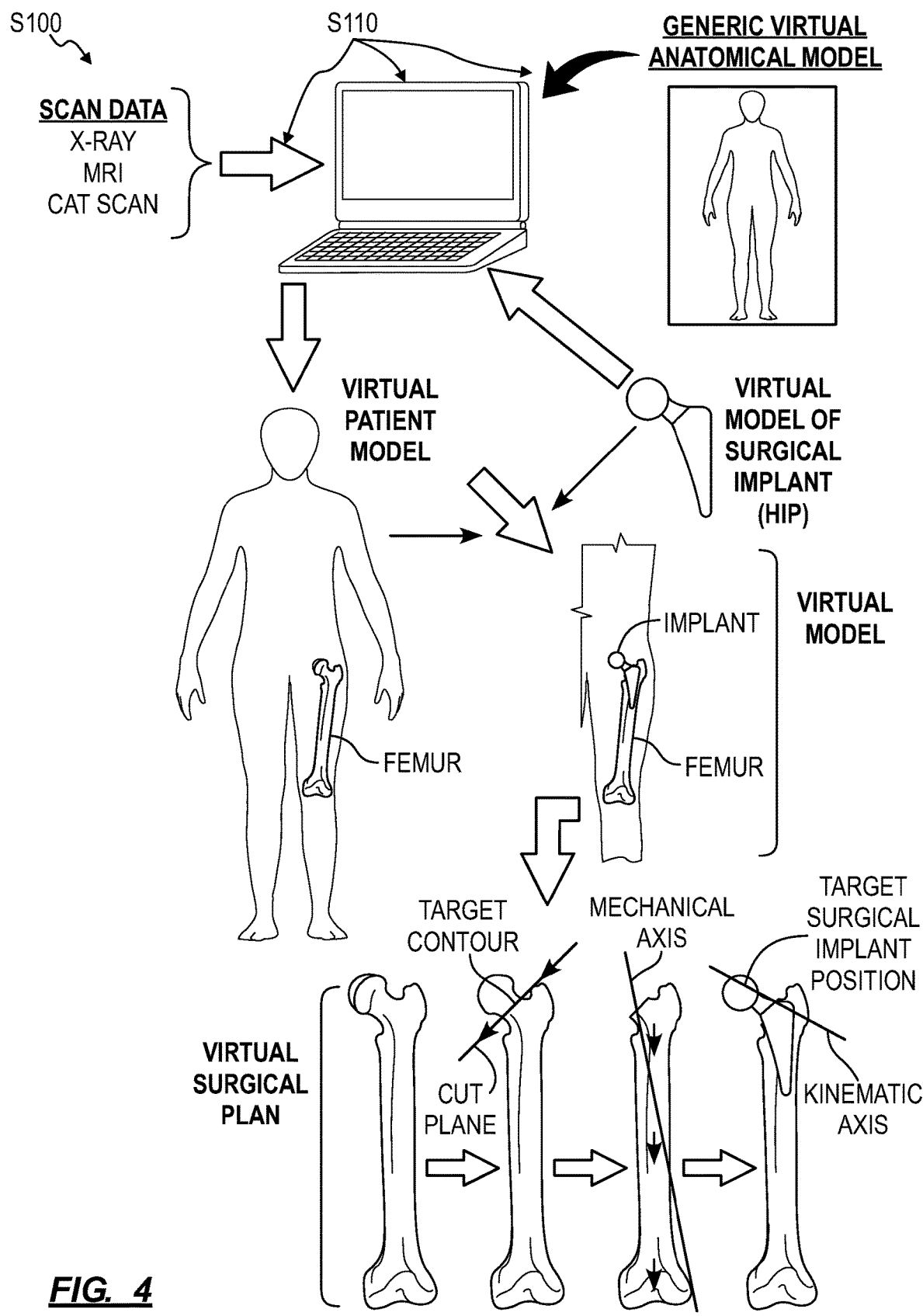
FIG. 4 is a flowchart representation of one variation of the method.

One variation of the method S100 shown in FIGS. 3 and 4 includes Block S110, which recites, prior to the surgical operation: accessing a pre-operative scan of the hard tissue of interest of the patient; extracting a virtual representation of the unresected contour of the hard tissue of interest from the pre-operative scan; generating a virtual representation of the target resected contour of the hard tissue of interest based on the virtual unresected contour of the hard tissue of interest and a pre-operative surgical plan defined by the surgeon; compiling the virtual representation of the unresected contour of the hard tissue of interest and the virtual representation of the target resected contour of the hard tissue of interest into the virtual patient model; and storing the virtual patient model, in association with the patient, in a database. Generally, in Block S110, the computer system can: access two-dimensional ("2D") or three-dimensional ("3D") MRI, CAT, X-ray (radiograph), or other scan data of all or a section of a patient's body designated for an upcoming surgery; and generate a virtual patient model of the patient based on these the scan data.

In one implementation, the computer system transforms pre-operative scan data (e.g., MRI scans, orthogonal X-rays images, and/or CT scans) of a hard tissue of interest into a virtual patient model representing the hard tissue of interest. For example, the computer system can access an MRI scan of a patient's left leg, including dimensionally-accurate details of bones (e.g., a femur and a tibia), tendons (e.g., a patellar tendon), ligaments (e.g., an anterior cruciate ligament), muscles (e.g., a quadriceps), other soft tissue (e.g., arteries, veins), and an envelope (e.g., a 2D silhouette or 3D skin surface profile) of the left leg. From the MRI scan, the computer system can generate a virtual scale representation of the patient's left leg, such as in the form of a virtual patient model that includes a dimensionally-accurate contour, surface, and/or volumetric anatomical hard tissue and soft tissue features of the patient's left leg.

In a similar implementation, the computer system can transform scan data into a virtual patient model of the patient's body according to an absolute scale for each bone, ligament, muscle, and/or other features represented within the scan data. Thus, the computer system can extract from the virtual patient model major dimensions, minor dimensions, contours, curvatures, etc. of anatomical components represented within the virtual patient model. For example, the computer system can combine orthogonal X-ray radiographs of a patient with a generic (parameterized) anatomical virtual patient model of a human anatomy. In order to yield a custom (patient-specific) virtual anatomical model reflective of the patient's anatomy, the computer system can extract a first point from the set of orthogonal radiographs corresponding to a first discrete location of the hard tissue of interest and query the generic virtual anatomical model for a first virtual point in the generic virtual anatomical model corresponding to the first point from the set of orthogonal radiographs. The first virtual point can be located in the generic virtual anatomical model by pattern matching the orthogonal radiographs with the generic virtual anatomical model to find similar geometry patterns (and shapes). In this example, the first point can be aligned adjacent a tibial plateau of the patient's tibia. The computer system can identify a shape of the tibial plateau in the orthogonal radiographs by matching a similar shape of a tibial plateau in the generic anatomical model. The computer system can then locate the first virtual point relative to geometric features of the tibia in the generic virtual patient model by identifying proximity of the first point to geometric features of the tibia in the orthogonal radiographs. The computer system can further extract a second point from the set of orthogonal radiographs corresponding to a discrete location of the hard tissue of interest; and define a second virtual point in the generic virtual anatomical model corresponding to the second point from the set of orthogonal radiographs. Based on a distance between the first and second points in the orthogonal radiographs, the computer system can scale the generic virtual anatomical model to define the custom virtual anatomical model by scaling a virtual distance between the first virtual point and the second virtual point in the custom virtual anatomical model to correspond to the real distance between the first point and the second point in the set of orthogonal scans. Thus, a virtual distance between the first virtual point and the second virtual point can be proportional to the real distance in the set of orthogonal scans.

In another implementation, the computer system can implement template matching techniques to match template tissue point clouds—labeled with one or more anatomical tissue labels—to tissue masses identified in the 3D point cloud and transfer anatomical tissue labels from matched template tissue point clouds to corresponding tissue masses in the 3D point cloud. Yet alternatively, the computer system can: implement computer vision techniques, such as edge detection or object recognition, to automatically detect distinct tissue masses in the scan data; present these distinct tissue masses in the scan data to the surgeon through the physician portal; and write an anatomical tissue label to each distinct tissue mass in the 3D point cloud based on anatomical tissue labels manually entered or selected by the surgeon through the physician portal. However, the computer system can implement any other method or technique to label tissues within patient scan data automatically or with guidance from a surgeon.

In one variation, a reference marker of known dimension is placed in the field of view of the scanner when the MRI, CAT, X-ray, or other scan data of the region of the patient's body is recorded. For example, three 1"-diameter steel spheres can be placed at different (X, Y, Z) positions around a patient's left knee when the patient's left knee is imaged in an MRI scanner. When analyzing an MRI scan to generate a surgical plan, the computer system can interpolate real dimensions of the patient's tissues (e.g., general and feature-specific length, width, depth of the tibia, femur, patella, tibial condyle, and femoral condyle, etc.) based on known dimensions of the reference marker(s). The computer system can label regions of patient tissues with these dimensions and/or can scale or modify the virtual patient model into alignment with these dimensions extracted from the patient scan data.

In another variation, by assembling data from a plurality of scans capturing anatomical components (i.e., a joint) of the patient's body in various positions, the computer system can extract a range of motion and relative angles between anatomical components represented in the scans. Then, the computer system can define ranges of motion and relative angles between virtual anatomical components represented in the virtual patient model accordingly. From the virtual patient model, the computer system can define constraint parameters and extract reasonable (or plausible) positions of the anatomical components in real space and, therefore, facilitate registration of the anatomical components as described below. For example, the computer system can access scan data of a knee (and areas surrounding the knee) bent to 30°, 45°, 90°, and 120°. Based on the scans, the computer system can extract data such as varus and/or valgus articulation of the tibia relative to the femur; degree of hyperextension of the tibia relative to the femur; and/or range of motion of the knee (e.g., between thirty to ninety degrees). The computer system can then input this data as a parameter for the virtual patient model, such that the virtual patient model reflects anatomical dimension, articulation, contours, range of motion, etc.

However, the computer system can transform any other scan data into a virtual patient model or other virtual and/or parametric representation of the patient's hard tissue of interest in any other way.

4.1 Virtual Patient Model Layers

In one variation shown in FIG. 4, the computer system stores anatomical and surgical plan data in a set of layers in the virtual patient model. For example, the virtual patient model can include: a first layer containing a 3D representation of the patient's bone structure around the hard tissue of interest; a second layer containing a 3D representation of the patient's cartilage structure around the hard tissue of interest; a third layer containing a 3D representation of the patient's musculature and ligature around the hard tissue of interest; a fourth layer containing a 3D representation of the patient's skin surface profile around the hard tissue of interest; a fifth layer containing a 3D representation of a surgical guide located at a target position on the patient's hard tissue of interest prior to resection of the hard tissue of interest; a sixth layer containing a 3D representation of the patient's hard tissue of interest following resection of this hard tissue of interest according to the predefined surgical plan; a seventh layer containing a 3D representation of a target position and orientation of a surgical implant relative to the patient's hard tissue of interest as specified in the predefined surgical plan; etc., such as for each hard tissue of interest (e.g., both a femur and a tibia) specified for the surgery. As described below, the computer system can then selectively enable and disable these layers presented on a display in the operating room, such as through a wall-mounted display or augmented reality headset worn by a surgeon in the operating room (or via a virtual reality headset worn by a remote physician or student).

Therefore, in this implementation, the computer system can: access a pre-operative scan of the patient's hard tissue of interest (e.g., a femur and a tibia); extract a three-dimensional contour of the hard tissue of interest from the pre-operative scan; extract a three-dimensional constellation of soft tissue features of the patient from the pre-operative scan; compile the three-dimensional contour of the hard tissue of interest and the three-dimensional constellation of soft tissue features of the patient into the virtual patient model; and store the virtual patient model—in association with the patient—in a database. Later, the computer system can access this virtual patient model from the database during the surgical operation on the patient.

In this variation, the computer system can also: track surgical steps—such as reorientation of the patient or a portion of the patient, incision into the patient's body, excision of a tissue within the patient's body, installation of a surgical implant, etc.—throughout the surgical operation, as described below; and selectively enable and disable layers of the virtual patient model accordingly.

In one example, the computer system can: register the first layer of the virtual patient model to the hard tissue of interest of the patient detected during the subsequent surgery prior to resection of the hard tissue of interest; derive a spatial relationship between features in the virtual patient model and intermediate features detected on the patient and near the hard tissue of interest prior to resection of the hard tissue of interest; and then preserve spatial alignment between the virtual patient model and the patient based on these intermediate features (and any hard tissue of interest features still present) following resection of the hard tissue of interest. The computer system can then selectively enable and disable layers in the virtual patient model based on current step of the surgical operation, such as by: enabling the first layer exclusively following resection of the hard tissue of interest in order to communicate a difference between the original hard tissue of interest (depicted virtually) and actual resection of the hard tissue of interest visible in the surgical field; enabling the fifth layer exclusively following resection of the hard tissue of interest in order to communicate a difference between the target resected profile of the hard tissue of interest (depicted virtually) defined in the surgical plan and actual resection of the hard tissue of interest visible in the surgical field; and enabling the sixth layer exclusively following installation of a surgical implant on or near the hard tissue of interest in order to communicate a difference between the target placement of the surgical implant (depicted virtually) relative to the hard tissue of interest and the actual placement of the surgical implant on the hard tissue of interest visible in the surgical field.

5. Optical Scans

Block S120 of the method S100 recites, during a first period of time succeeding incision of the patient proximal the hard tissue of interest and prior to resection of the hard tissue of interest within a surgical operation, accessing a first sequence of optical scans recorded by an optical sensor facing the surgical field occupied by the patient. Generally, in Block S120, the computer system can interface with one or more cameras or other sensors to collect optical scan data and/or other data representative of a surgical field occupied by the patient, as shown in FIGS. 1A and 2.

In one implementation, the computer system can interface with a single optical sensor (e.g., an infrared, LIDAR, depth and/or any other optical sensor), such as a forward-facing camera arranged on an augmented reality headset worn by a surgeon within the surgical field. In another implementation, the computer system can interface with an array of optical sensors arranged at various locations of the surgical field (e.g., worn by a surgeon, a technician, a nurse, a surgical resident, or an anesthesiologist, or arranged at discrete static locations such as over the surgical field, adjacent a monitor within the surgical field, etc.). In this implementation, the computer system can access optical scan data from each optical sensor in the array of optical sensors and stitch together the optical scans to generate a three-dimensional (or "3D") panoramic image of the surgical field. The computer system can then render the 3D image onto a display, such as a heads-up (or eyes-up) display integrated into an augmented reality headset worn by a surgeon, so that the surgeon may view the 3D image of the surgical field from her natural perspective within the surgical field and/or from any other perspective selected by the surgeon (e.g., from the perspective of a surgical resident or technician on an opposite side of the surgical field from the surgeon). (The computer system can similar generate and serve virtual reality frames depicting similar content to a virtual reality headset worn by a remote physician or student, such as in real-time.)

For example, the computer system can download digital photographic color images from a forward-facing camera or optical sensor arranged on each side of an augmented reality headset worn by a surgeon during the surgical operation. In another example, the computer system can download digital photographic color images from multiple downward-facing cameras arranged in a fixed location over an operating table within an operating room. In these examples, the computer system (or a remote computer contracted by the computer system) can stitch optical scans captured substantially simultaneously by two or more cameras within the operating room into a 3D point cloud or other 3D image of a volume within the operating room (hereinafter "3D surgical field image").

In a similar implementation, the computer system can: access a first sequence of color images from a fixed stereo camera arranged over and facing an operating table within the surgical field; transform the first sequence of color images into a first set of three-dimensional color point clouds; and combine the first set of three-dimensional color point clouds into a composite three-dimensional color point cloud depicting hard tissue and soft tissue of the patient in Block S120. Based on the composite three-dimensional color point cloud, the computer system can then detect the hard tissue of interest in Block S132 and select the set of intermediate features in the Block S136, as described below.

The computer system can additionally or alternatively download distance data, such as in the form of a 3D point cloud output by a LIDAR sensor arranged over the operating table. The computer system can further merge digital photographic color images with distance data to generate a substantially dimensionally-accurate color map of a volume within the operating room.

The computer system can collect these optical scan data in Block S120 and process these optical scan data as described below substantially in real-time. The computer system can collect optical scans from one or more cameras—in fixed locations or mobile within the surgical field—or distance data from one or more other sensors at a frame rate similar to a projection frame rate of the augmented reality device, such as thirty frames per second. However, the computer system can collect any other color, distance, or additional data from any other type of sensor throughout a surgery.

5.1 Feature Detection

In one implementation shown in FIGS. 1A and 3, the computer system can implement edge detection, template matching, and/or other computer vision techniques to process the 3D surgical field image to identify a human feature (e.g., a skin feature, the hard tissue of interest) in the real surgical field in Block S140 and can then align the virtual patient model to the human feature within the virtual surgical environment. By thus mapping a virtual patient model within the virtual surgical environment onto real patient tissue identified in the 3D surgical field image, the computer system can later generate an augmented reality frame containing virtual features aligned to real patient tissue in the surgical field, such as by projecting the virtual surgical environment onto the surgeon's known or calculated field of view, as described below.

In one example, the computer system can: transform 2D optical scans captured by cameras within the operating room into a 3D surgical field image; identify the patient's left leg in the 3D surgical field image; and map the virtual patient model of the patient's left leg transformed from scan data of the patient's left leg onto the patient's left leg in the 3D surgical field image. In this example, the computer system can implement object detection, edge detection, surface detection, and/or any other computer vision technique to distinguish distinct volumes or surfaces in the 3D surgical field image. The computer system can then compare the virtual patient model to distinct volumes or surfaces in the 3D surgical field image to identify the patient's lower left leg represented in the 3D surgical field image. Similarly, the computer system can compare the virtual patient model to these distinct volumes or surfaces in the 3D surgical field image to identify the patient's left thigh represented in the 3D surgical field image.

In the foregoing implementation, the computer system can compare various tissue types in the virtual patient model and in the 3D surgical field image to align the virtual patient model to the 3D surgical field image. In particular, the computer system can implement edge detection, color matching, texture recognition, and/or other computer vision techniques to distinguish skin, muscle, bone, and other tissue in the 3D surgical field image. Therefore, the computer system can: associate a smooth, non-geometric surface with skin; associate a rough red surface inset from a skin surface with muscle; and associate a smooth, light pink or (near-) white surface inset from both skin and muscle surfaces as bone. The computer system can then label points or surfaces in the 3D surgical field image accordingly. The computer system can therefore detect different types of tissue within the surgical field and dynamically map the virtual patient model to one or more tissue types throughout a surgery as the patient's body is manipulated and as different tissues are exposed.

The computer system can also identify and characterize substantially unique tissue features and contours within the patient's scan data. For example, for scan data of a patient designated for an upcoming hip surgery, the computer system can characterize the size and geometry of the cotyloid fossa of the patient's acetabulum and then reference surgical operations on the patient's hip in the surgical plan to these unique features of the patient's cotyloid fossa. Later, during the operation, the computer system can: detect such features on the patient's cotyloid fossa in a feed of images of the surgical field when the patient's hip is opened and the cotyloid fossa is exposed; and orient (or align) a virtual patient model of the acetabulum to the cotyloid fossa shown in the optical scan feed. In another example, the computer system can access scan data recorded by a multispectral camera in the operating room and distinguish different hard and soft tissues in the surgical field based on different multispectral signatures of these tissues; the computer system can then project boundaries of different tissues identified in these multispectral data onto a concurrent depth image to isolate and extract 3D geometries of these different hard and soft tissues from the depth image.

In one variation, the computer system can sequentially detect objects within the surgical field according to a hierarchy. For example, the computer system can sequentially detect objects in an optical scan of the surgical field in the following order: an operating table; the patient and a hard tissue of interest of the patient; a soft tissue component within the hard tissue of interest of the patient; vascular features of the patient; neuromuscular components; and, finally, a hard tissue of interest (e.g., a bone or subset of bones). Alternatively, the computer system can selectively detect objects in the optical scan of the surgical field in any order.

Alternatively, the computer system can detect and identify a particular confirmation gesture performed by the surgeon, nurse, or other human within the surgical field to locate a particular feature of the patient within the surgical field. For example, the computer system can detect, in the optical scan of the surgical field or in the field of view of the surgeon, a gloved hand (e.g., a blue glove) contacting a surface within the surgical field. The computer system can then identify the contact with the surface as confirmation that an overlay frame depicting the virtual patient model of the patient is properly aligned with the patient (i.e., the surface the surgeon contact). For example, the computer system can identify contact by a gloved hand with a leg as alignment with a correct leg (i.e., a leg the surgeon may prepare for surgery).

Furthermore, as described above, the computer system can extract range of motion and articulation information for anatomical components from the virtual patient model; define registration parameters for registering objects within the surgical field as a hard tissue of interest depicted within the virtual patient model; and then locate objects within the surgical field that conform to the registration parameters. For example, the computer system can access scan data that depicts a three-degree valgus articulation deformity between the tibia and the femur at a patient's left knee. Then the computer system can scan the surgical field for an object with a three-degree valgus articulation. The computer system can ignore features and objects within the surgical field without a three-degree valgus articulation and, thus, expedite alignment between the virtual patient model and the patient's left knee.

However, the computer system can implement any other method or technique to detect a surface or volume corresponding to a region of a patient's body to align a virtual patient model of the patient to the region of a patient's body in the real surgical environment. The computer system can also repeat the foregoing process for each optical scan retrieved in Block S120 substantially in real-time throughout the surgical operation.

6. Pre-Incision: Coarse Registration

In one variation shown in FIGS. 1A and 3, the computer system coarsely registers the virtual patient model to the hard tissue of interest in the surgical field based on patient features detected in optical scans prior to the surgeon incising the patient near the hard tissue of interest and/or prior to exposure of the hard tissue of interest.

In one implementation, during an initial period of time preceding exposure of the hard tissue of interest within the surgical operation, the computer system: accesses an initial sequence of optical scans recorded by the optical sensor; detects a head of the patient in the initial sequence of optical scans; detects a foot in the initial sequence of optical scans; derives an orientation of the patient relative to the optical sensor based on locations of the patient's head and foot in the initial sequence of optical scans; scans regions of the initial sequence of optical scans near the detected head for a face or eyes of the patient to determine whether the patient is lying on her front or back; and predicts a region of the surgical field occupied by the hard tissue of interest based on the orientation of the patient and a human anatomy model. The computer system then scans the region in the surgical field depicted in the initial sequence of optical scans for a soft tissue (e.g., skin near the patient's left knee) proximal the hard tissue of interest (e.g., the patient's left femoral condyle and left tibial plateau). Upon detecting soft tissue features in this region of the surgical field, the computer system can then coarsely register the virtual patient model to these soft tissue features, such as including orienting the virtual patient model based on the detected orientation of the patient (e.g., to set the longitudinal axis of the virtual patient model parallel to the longitudinal axis of the patient's torso).

For example, in Block S110, the computer system can generate a virtual scale representation of the patient's left leg, such as in the form of a virtual patient model that includes a dimensionally-accurate contour, surface, and/or volumetric anatomical hard tissue and soft tissue features of the patient's left leg based on an MRI scan of the patient's left leg. During a subsequent surgery, the computer system can map the virtual patient model to real features of the patient's body—detected in optical scan data (e.g., 2D or 3D color images) recorded by an optical sensor facing the surgical field—in order to anticipate locations, dimensions, and contours, etc. of both visible and obscured anatomical features (e.g., a patella, a tibial head, or other sub-dermal tissues) of the patient. In particular, prior to a first incision into the patient during the surgical operation, the computer system can access a video feed of a surgical field from an optical sensor arranged overhead the operating table (or from a camera arranged on an augmented reality headset worn by a surgeon); detect the operating table, a human body, a head or face, feet, and a side of the body facing the optical sensor; derive an orientation of the patient's body relative to the camera based on the position of the head or face and feet; predict a location of the hard tissue of interest (e.g., the patient's left leg) in the field of view of the optical sensor; and scan this location for a leg. Upon detecting a leg in this location, the computer system can coarsely register the virtual patient model of the patient's left leg to the detected leg in the surgical field. The computer system can initially refine this coarse registration by calculating a best fit of a 3D skin surface contour or envelope represented in the virtual patient model to a contour of the leg detected in the surgical field.

However, the computer system can implement any other method or technique to coarsely register the virtual patient model to the patient.

7. Joint Articulation and Mechanical Axis Reconstruction

In one variation shown in FIG. 1A, the computer system calculates a mechanical axis of the hard tissue of interest. For example, the computer system can: track a constellation of features (e.g., skin features, intermediate features described below) on the patient in a sequence of optical scans prior to resection of the hard tissue of interest; detect movement of these features within these optical scans; and then derive a real mechanical axis of the hard tissue of interest from movement of these features, such as by calculating a best-fit line that preserves relative positions of features in the constellation over a range of positions of the patient's hard tissue of interest detected in these optical scans.

In one implementation, the computer system serves a prompt to a surgeon in the surgical field to manipulate a portion of the patient proximal the hard tissue of interest through a range of motion during a period of time. As the patients move the portion of the patient (e.g., the patient's left hip joint, left knee, and left ankle) through this range of motion, the computer system can: record a sequence of optical scans; track motion of the patient's upper left leg (e.g., superficial soft tissue features on patient's upper left leg) relative to the patient's hip or lower torso in these optical scans; and derive a joint center of rotation of the patient's left hip relative to the patient's lower torso. Similarly, as the surgeon articulates the patient's left knee joint, the computer system can: track motion of patient's upper leg relative to her lower leg; derive a joint center of rotation of the patient's left knee relative to superficial soft tissue features on the patient's left leg; and/or derive a mechanical axis of the patient's left femur, such as by calculating a line—referenced to the soft tissue features of the patient (and later to hard tissue features of the patient)—that intersects both the joint center of rotation of the patient's left hip and the joint center of rotation of the patient's left knee. Furthermore, as the surgeon rotates the patient's left ankle joint, the computer system can track motion of the patient's left foot relative to her left lower leg; derive a joint center of rotation of the patient's left ankle joint relative to superficial soft tissue features the patient's left leg and left foot; and/or derive a mechanical axis of the patient's tibia, such as by calculating a line—referenced to the soft tissue features of the patient (and later to hard tissue features of the patient)—that intersects both the joint center of rotation of the patient's left knee and the joint center of rotation of the patient's left ankle.

Alternatively, the computer system can passively track these features in the surgical field as the surgeon prepares the patient for incision on the operating table and then implement the foregoing methods and techniques to derive mechanical axes of hard tissue in the patient's left leg. The computer system can similarly derive a kinematic axis of rotation of the patient's knee.

The computer system can then further refine course registration of the virtual patient model to the patient by aligning a virtual mechanical axis of the hard tissue of interest—defined in the virtual patient model—with the corresponding (real) mechanical axis derived from optical scan data recorded during the surgery, such as by aligning both: the mechanical axis of a virtual femur in the virtual patient model to the mechanical axis of the patient's femur thus identified in the surgical field; the kinematic axis of a virtual leg in the virtual patient model to the kinematic axis of the patient's knee thus identified in the surgical field.

The computer system can implement similar methods and techniques to detect mechanical axes, anatomical axes, and/or kinematic axes of the patient's tissue of interests, such as: an anatomical axis of the patient's femur; an anatomical axis of the patient's tibia; a mechanical axis of the patient's femur; a mechanical axis of the patient's tibia; and/or a mechanical axis of the patient's femur; and a mechanical or kinematic axis of the patient's leg (e.g., from hip to ankle) for a total knee replacement surgery. The computer system can then refine course registration of the virtual patient model to the patient by aligning a virtual anatomical, mechanical, and/or kinematic axes of the hard tissue of interest—defined in the virtual patient model—with the corresponding axis derived from optical scan data recorded during the surgery.

8. Post-Incision: Coarse Registration Confirmation

Furthermore, once the surgeon incises the patient near the hard tissue of interest, the computer system can detect this incision to verify coarse registration of the virtual patient model.

In one implementation, after incision of the patient proximal the hard tissue of interest, the computer system can: continue to access or record optical scans of the surgical field; detect presence of a red surface (e.g., red pixels, which may depict blood or muscle tissue) in this sequence of optical scans; and confirm registration of the virtual patient model to soft tissue features proximal the unexposed hard tissue of interest if the location of this detected red surface intersects the virtual patient model thus coarsely registered to the patient.

In particular, presence of red pixels in the surgical field may indicate blood or muscle tissue near the hard tissue of interest. Therefore, if the computer system detects red pixels near the virtual hard tissue of interest depicted in the tissue virtual patient models coarsely-registered to the patient, the computer system can verify this coarse registration of the virtual patient model.

9. Post-Incision: Hard Tissue of Interest Features

Blocks S130, S132, and S134 recite: accessing a first sequence of optical scans recorded by an optical sensor facing a surgical field occupied by the patient; detecting a first contour of the hard tissue of interest in the first sequence of optical scans; and registering virtual hard tissue features defined in the virtual patient model to the first contour of the hard tissue of interest, respectively. Generally, in Blocks S130, S132, and S134, the computer system can: detect the unresected contour of the hard tissue of interest—once exposed by the surgeon following incision into nearby soft tissue—in a sequence of optical scans of the surgical field; and then refine registration of the virtual patient model to the patient by aligning virtual hard tissue of interest features defined in the virtual patient model to real hard tissue of interest features detected in these optical scans. In particular, in Blocks S130, S132, and S134, the computer system can refine coarse registration of the virtual patient model to the hard tissue of interest, such as based on alignment of virtual hard tissue features defined in the virtual patient model and an unresected contour of the hard tissue of interest detected in the surgical field, as shown in FIGS. 1A, 2, and 3.

In one implementation, the computer system can scan a region in a sequence of optical scans that intersects the coarsely-registered virtual patient model for exposed hard tissue (e.g., a real unresected contour of a real femoral condyle), such as depicted by white pixels (e.g., bone) surrounded by red pixels in these optical scans. When a hard tissue surface is thus detected, the computer system can: extract a 3D surface profile of the exposed hard tissue from this sequence of optical scans, such as by implementing methods and techniques described above and below; confirm that this 3D surface profile approximates a geometry of a virtual hard tissue of interest defined in the virtual patient model (e.g., either a tibial plateau or a femoral condyle); and, if so, extract representative features from this 3D surface profile of the exposed hard tissue of interest. The computer system can then: match these representative features of the real hard tissue of interest to like virtual hard tissue of interest features defined in the virtual patient model (e.g., a virtual unresected contour of a virtual femoral condyle derived from a pre-operative scan of the patient's knee and stored in the virtual patient model); and snap these virtual hard tissue of interest features to their corresponding real hard tissue of interest features in order to register the virtual patient model to the patient.

In a similar implementation, the computer system can: derive the actual mechanical axis of the hard tissue of interest (e.g., the mechanical axis of the patient's femur) thus detected in the surgical field, as described above; align (or "snap") a virtual mechanical axis of the hard tissue of interest defined in the virtual patient model to the actual mechanical axis of the hard tissue of interest detected in the surgical field, thereby virtually constraining the virtual patient model to the patient in four degrees of freedom; and then snap virtual hard tissue features defined in the virtual patient model to the unresected contour of the hard tissue of interest detected in the surgical field. In particular, the computer system can translate and rotate the virtual patient model to a position relative to the hard tissue of interest detected in the surgical field that minimizes error (e.g., offset) between virtual hard tissue of interest features in the virtual patient model and corresponding real hard tissue of interest features detected in the surgical field, thereby constraining the virtual patient model to the patient in six total degrees of freedom.

9.1 Example: Femur

In one example implementation, the virtual patient model includes a virtual representation of the patient's unresected femur, which defines a hard tissue of interest for the surgery. In this example implementation, the computer system can: detect an unresected contour of a femoral condyle of the patient in the current sequence of optical scans; and then register virtual unresected femoral condyle features defined in the virtual patient model to the unresected contour of the femoral condyle detected in this sequence of optical scans.

For example, the computer system can: detect exposed bone near a coarsely-registered virtual patient model of the patient's left leg in a sequence of optical scans; extract a 3D surface profile of this exposed bone from these optical scans; and identify this exposed bone as lateral and medial femoral condyles, such as based on similarity between this 3D surface profile and a generic femoral condyle model or similarity between this 3D surface profile and virtual femoral condyles represented in the virtual patient model. The computer system can then snap a virtual 3D surface profile (or constellation of femoral condyle features) of the femoral condyle represented in the virtual patient model to the 3D surface profile of the exposed bone (or constellation of features representative of the exposed bone) in order to refine alignment and minimize error between the virtual femur in the virtual patient model and the real hard tissue of interest in the surgical field.

In this example, the computer system can also verify alignment between the mechanical axis of the virtual femur depicted in the virtual patient model and the real mechanical exit derived from motion of the patient's left leg during the surgery, as described above.

9.2 Example: Tibia

The computer system can implement similar methods and techniques to register a virtual representation of the patient's unresected tibia to another exposed bone surface in the surgical field. In this example implementation, the virtual patient model can also include a virtual representation of the patient's unresected tibia, which defines a second hard tissue of interest for the surgery. The computer system can therefore: detect an unresected contour of a tibial plateau of the patient in the current sequence of optical scans; and then register virtual unresected tibial plateau features defined in the virtual patient model to the unresected contour of the tibial plateau detected in this sequence of optical scans.

For example, the computer system can: detect a second exposed bone near a coarsely-registered virtual patient model of the patient's left leg in the same sequence of optical scans described above; extract a 3D surface profile of this second exposed bone from these optical scans; and identify this exposed bone as a tibial plateau, such as based on similarity between this 3D surface profile and a generic tibial plateau model or similarity between this 3D surface profile and a virtual tibial plateau represented in the virtual patient model. The computer system can then snap a virtual 3D surface profile (or constellation of femoral condyle features) of the tibial plateau represented in the virtual patient model to the 3D surface profile of the second exposed bone (or constellation of features representative of the second exposed bone) in order to refine alignment and minimize error between the virtual tibia in the virtual patient model and this second hard tissue of interest in the surgical field.

The computer system can therefore: register a virtual femur in the virtual patient model to a femoral condyle detected in the surgical field; separately register a virtual tibia in the virtual patient model to a tibial plateau detected in the surgical field; and virtually articulate the virtual tibia relative to the virtual femur in the virtual patient model responsive to real changes in angular position of the patient's lower leg relative to the patient's upper leg.

9.3 Virtual Patient Model Correction

In one variation, the computer system modifies the virtual patient model in order to further minimize or eliminate error between a virtual contour of the hard tissue of interest represented in the virtual patient model and the actual contour of the hard tissue of interest detected in the surgical field. In particular, prior to resection of the hard tissue of interest, the computer system can interpret the actual hard tissue of interest detected in the surgical field as a "ground truth" of the patient's original tissue and then drive the virtual patient model into alignment with this ground truth.

In one implementation, the computer system: calculates a best-fit location of the virtual patient model, relative to the hard tissue of interest, that minimizes error between virtual hard tissue features defined in the virtual patient model and the unresected contour of the hard tissue of interest detected in a sequence of optical scans; and then displaces these virtual hard tissue features defined in the virtual patient model into alignment with the unresected contour of the hard tissue of interest detected in these optical scans. Similarly, the computer system can: extract a 3D surface profile of the exposed, unresected hard tissue of interest from optical scans of the surgical field; align the virtual patient model to the patient such that error between a virtual unresected contour of this hard tissue of interest in the virtual patient model and the 3D surface profile of the exposed, unresected hard tissue of interest is minimized (and such that error between virtual and derived mechanical axes of the hard tissue of interest is minimized); and then deform the virtual unresected contour of this hard tissue of interest in the virtual patient model into 3D superficial alignment with the 3D surface profile of the exposed, unresected hard tissue of interest detected in the surgical field.

Therefore, the computer system can detect differences between hard tissue contours detected in the surgical field and like contours depicted in the virtual patient model and then adjust the virtual patient model to reflect these hard tissue contours detected in the surgical field. For example, the virtual patient model can include a virtual femur defined by a set of perpendicular 3D contour lines. The computer system can thus implement methods and techniques described above to calculate a best fit location of the virtual femur in the virtual patient model that minimizes distances from vertices of these perpendicular 3D contour lines to the 3D surface profile of the femoral condyle detected in the surgical field. The computer system can then adjust (or "snap") these vertices at intersections of these 3D contour lines defining the virtual femur onto the 3D surface profile of femoral condyles detected in the surgical field.

In this foregoing implementation, the computer system can: characterize the deformation of the virtual unresected contour of the hard tissue of interest in the virtual patient model that aligns this virtual unresected contour to the actual unresected contour of the hard tissue of interest features detected in the surgical field; and then apply this deformation to other virtual hard tissue of interest representations in the virtual patient model, such as: a virtual target resected contour of the hard tissue of interest in the virtual patient model; and a virtual representation of a target position of a surgical implant on the hard tissue of interest in the virtual patient model. Therefore, the virtual patient model can include multiple layers of representations of various steps of the surgery, as described above; and the computer system can deform each of these layers into alignment with the actual unresected contour of the hard tissue of interest detected in the surgical field.

9.4 Generic Virtual Anatomical Model

In a similar variation, the virtual patient model includes a virtual anatomical model containing a generic representation of the hard tissue of interest. In this variation, the computer system can implement similar methods and techniques to calculate a best-fit location of the virtual anatomical model, relative to the hard tissue of interest, that minimizes error between virtual hard tissue features defined in the virtual anatomical model and the unresected contour of the hard tissue of interest detected in the first sequence of optical scans. The computer system can then deform (or morph) the generic representation of the hard tissue of interest into conformity with the unique anatomy of the patient by displacing virtual hard tissue features defined in the virtual anatomical model into alignment with the unresected contour of the hard tissue of interest detected in the first sequence of optical scans.

Therefore, in this variation, the computer system can register a generic virtual anatomical model to the patient and virtually deform this generic virtual anatomical model into alignment with hard tissue of interest features detected in the surgical field, thereby generating a virtual patient model unique to the patient prior to resection of the hard tissue of interest during the surgery, such as if no pre-operative scan of the patient's hard tissue of interest is available.

9.5 Ad Hoc Surgical Plan

In another variation, the computer system can define a target resected contour for the hard tissue of interest during the surgery, such as after the hard tissue of interest is exposed and before the hard tissue of interest is resected (and once a generic virtual anatomical model is aligned to the patient's unique anatomy, as described above). For example, once the generic virtual anatomical model is aligned to the patient's unique anatomy, the computer system can receive a command from the surgeon specifying a set of target resection parameters for the hard tissue of interest, such as a sequence of quantitative resection parameters—for a type of the surgery—spoken by the surgeon orally or entered manually into a touchscreen, touchpad, or other user interface in or near the surgical field. The computer system can then: project this set of target resection parameters onto the virtual representation of the unresected contour of the hard tissue of interest to define a target resected contour of the hard tissue of interest; and then store the target resected contour of the hard tissue of interest in the virtual patient model.

Therefore, the computer system can ingest target resection parameters for the surgery and then generate a virtual representation of the target resected contour of the hard tissue of interest accordingly in real-time during the surgery.

Similarly, the computer system can: ingest commands for position of a surgical implant on the hard tissue of interest; project a virtual representation of the surgical implant onto the virtual patient model according to these commands to define a virtual representation of the hard tissue of interest with implant; subtract a virtual volume of this surgical implant from the virtual unresected contour of the hard tissue of interest to generate a virtual representation of the target resected contour of the hard tissue of interest; and then store both the virtual representation of the hard tissue of interest with implant and the virtual representation of the target resected contour of the hard tissue of interest.

10. Post-Incision: Intermediate Features

Block S136 of the method S100 recites detecting a set of intermediate features, on the patient and proximal the hard tissue of interest, in the first sequence of optical scans; and Block S140 of the method S100 recites deriving a spatial relationship between the set of intermediate features and the virtual patient model based on registration of the virtual patient model to the hard tissue of interest. Generally, in Block S136, the computer system can identify a set (or "constellation") of real features on and/or near the hard tissue of interest predicted to persist throughout the surgery (i.e., predicted to not be removed from the patient during the surgery), as shown in FIGS. 1A and 3. When the virtual patient model registers to hard tissue of interest in Block S134, the computer system can then calculate a spatial relationship between the virtual patient model and this set of real, persistent features (or "intermediate features") in Block S140. Later, as the hard tissue of interest is modified (e.g., resected, cut connected to a surgical implant) during the surgery, the computer system can transition to registering the virtual patient model to the hard tissue of interest via this set of real, persistent features rather than directly to the real hard tissue of interest.

For example, in Block S136, the computer system can aggregate a set of intermediate features that includes a constellation of visible skin features on the patient proximal the hard tissue of interest, such as: moles; freckles; bruises; veins; or notes or fiducials applied by medical staff with an ink marker. The computer system can also include the mechanical axis of the hard tissue of interest in this set of intermediate features and/or a surface profile or contour of the patient's skin near and offset from the exposed hard tissue of interest. In one variation, the computer system can also incorporate a 3D geometry of the resected contour of the tissue of interest in this set of intermediate features and leverage the resected contour to register the virtual patient model the patient's anatomy throughout the surgery, such as until the resected contour of the tissue of interest is obscured by an artificial component or again resected (at which time the computer system can update the set of intermediate features to reflect this anatomical change).

Furthermore, the computer system can project a virtual target resected contour of the hard tissue of interest onto the hard tissue of interest detected in the surgical field to identify a secondary surface on the hard tissue of interest predicted to remain unchanged during the surgery, extract bone features from this secondary surface, and append the set of intermediate features with these bone features. The computer system can also compile intermediate features that span all or a large segment of the circumference of the patient's appendage containing the hard tissue of interest, such as between a minimum distance (e.g., 20 centimeters) and a maximum distance (e.g., 50 centimeters) from the hard tissue of interest.

The computer system can then store a 3D spatial map of these intermediate features relative to the virtual patient model when the virtual patient model is registered to the hard tissue of interest. For example, the computer system can: generate a 3D map of the constellation of intermediate features detected in the surgical field; define an intermediate origin to this 3D map; assign a model origin to the virtual patient model; calculate a transform or quaternion that represents an offset between the intermediate origin and the model origin when the virtual patient model is registered to the patient's real hard tissue of interest; and store this transform or quaternion as the spatial relationship between these intermediate features, the hard tissue of interest, and the virtual patient model.

The computer system can implement this process for each hard tissue of interest specified in the virtual patient model. For example, during a total knee replacement surgery, the computer system can: define a first set of intermediate features and derive a first spatial relationship between a virtual femur model and the patient's (real, physical) femur; and similarly define a second set of intermediate features and derive a second spatial between a virtual tibia model and the patient's (real, physical) tibia.

Finally, once the computer system has registered the virtual patient model to the hard tissue of interest in the surgical field and defined a set of intermediate features and a spatial relationship that maps the virtual patient model to the hard tissue of interest, the computer system can serve confirmation of registration of the virtual patient model and patient features to the surgeon and then prompt the surgeon to execute a next step of the surgery (e.g., resection of the hard tissue of interest).

11. Registration Refinement Prior to Bone Resection

In one variation, the computer system repeats the foregoing methods and techniques throughout the surgery and prior to resection of the hard tissue of interest in order to collect additional patient tissue data and to compile these patient tissue data into a high-resolution, high-accuracy 3D representation of the patient's hard and soft tissue around the hard tissue of interest.

For example, during a scan cycle, the computer system can: record a first depth image or first stereoscopic color image via the optical sensor; detect the patient in a segment of the first image; and generate an initial 3D field representation of the patient based on soft tissue data contained in the segment of the first image. During a next scan cycle, the computer system can: record a second depth image or second stereoscopic color image; detect the patient in a segment of the second image; and augment the 3D field representation of the patient with soft tissue data contained in the segment of the second image. The computer system can repeat this process during a next sequence of scan cycles to refine the 3D field representation of the patient prior to incision near the hard tissue of interest. During a third, later scan cycle, the computer system can: detect incision of the patient based on presence of red pixels in the third image; detect the patient in a segment of the third image; and repeat the foregoing process to further augment the 3D field representation of the patient with soft tissue data contained in the segment of the third image (outside of the red region in the third image). The computer system can repeat this process during a next sequence of scan cycles to further refine the 3D field representation of the patient following incision and prior to resection of the hard tissue of interest.

During a fourth, later scan cycle, the computer system can: detect the hard tissue of interest (e.g., bone, such as a femoral condyle) based on presence of white pixels in the fourth image; detect the patient in a segment of the fourth image; repeat the foregoing process to augment the 3D field representation of the patient with soft tissue data contained in the segment of the fourth image (outside of the exposed bone and red soft tissue area of the fourth image); and inject hard tissue of interest data—depicting the location, orientation, and geometry of a bone surface (e.g., a femoral condyle, a tibial plateau) detected in the fourth image—into the 3D field representation of the patient such that these hard tissue of interest data are referenced to soft tissue features (and/or vice versa) in the 3D field representation of the patient. In this example, the computer system can repeat this process during a next sequence of scan cycles in order to further refine the 3D field representation of the patient, including both the patient's soft and hard tissue and references therebetween.

The computer system can therefore compile anatomical patient data extracted from a series of scan cycles into a more complete and accurate (e.g., low noise, high-fidelity) 3D virtual representation of the patient's hard and soft tissue around the hard tissue of interest by over a series of scan cycles.

The computer system can then implement methods and techniques described above to: register the virtual patient model to hard tissue depicted in this 3D field representation of the patient; select the set of intermediate features from the 3D field representation of the patient; and derive a spatial relationship between these intermediate features and the virtual patient model from this 3D field representation of the patient.

12. Resection

Once the virtual patient model is registered to the patient's hard tissue of interest and intermediate features, the surgeon may execute a next step of the surgery, such as by resecting a portion of the patient's exposed femoral condyle or tibial plateau according the surgical plan, as shown in FIGS. 1B and 2.

For example, the surgeon may install a physical guide on the patient and then manipulate a surgical tool along the physical guide to resect the patient's femoral condyle. In this example, the virtual patient model can include a layer defining a virtual target position of the surgical guide relative to the hard tissue of interest. The computer system can therefore implement methods and techniques described below and in U.S. patent application Ser. No. 15/594,623 to generate an augmented reality frame depicting a target location of the surgical guide—defined in the surgical plan—aligned to the hard tissue of interest in the surgeon's field of view of the surgical field. An augmented reality headset worn by the surgeon can then render this augmented reality frame in order to visually guide the surgeon in placing the surgical guide on the patient. Similarly, the computer system can implement methods and techniques described below to detect a difference between actual placement of the surgical guide and the target position of the surgical guide and prompt the user to make adjustments to the position of the surgical guide accordingly.

In another example, the virtual patient model includes a layer defining a target resected contour of the hard tissue of interest in the form of a virtual 3D representation of the hard tissue of interest. The computer system can therefore implement methods and techniques described below and in U.S. patent application Ser. No. 15/594,623 to generate an augmented reality frame depicting the target resected contour of the hard tissue of interest is aligned to the hard tissue of interest in the surgeon's field of view of the surgical field. An augmented reality headset worn by the surgeon can then render this augmented reality frame in order to visually guide the surgeon in either: placing the surgical guide on the patient; or manipulating a surgical tool along the augmented reality depiction of the target resected contour of the hard tissue of interest without a physical surgical guide in the surgical field.

Furthermore, the computer system can aggregate resected contour data (and surgical implant position data) collected during a surgery and similarly serve these data to a remote physician portal to enable a remote physician to track progress of the surgery and to return recommendations or prompts to the surgeon currently operating on the patient. For example, the computer system can generate augmented reality or virtual reality frames depicting the surgical field, such as both real tissues of interest and virtual representations of these hard tissues of interest, and then serve these to a computing device worn or accessed by a remote physician to enable the remote physician to "experience" the surgery, such as in (near) real-time. For example, the computer system can: select a frame in a sequence of optical scans; project a virtual representation of an unresected contour of the hard tissue of interest, defined in the virtual patient model, onto the frame; write a spatial difference between the actual resected contour and unresected contour (or target resected contour, etc.) to the frame; and then serve the frame to a physician portal—affiliated with a second surgeon located remotely from the surgical field—for remote monitoring of the surgery. The computer system can also enable the remote physician to control or alter parameters of the surgery based on deviations from the patient's preoperative anatomical state and/or deviations from the surgical plan—as depicted in these augmented or virtual reality frames served to the remote physician—such as by: setting virtual surgical stops; repositioning virtual objects (e.g., target positions of virtual artificial components, target resected contours) in the surgical plan; enabling or gating subsequent steps of the surgery; or controlling step-wise robotic execution of the surgical plan.

As the surgeon completes sequential steps of the surgical plan, the computer system can: preserve registration of the virtual patient model to the patients; and selectively activate (e.g., render) and deactivate (e.g., hide) layers of the virtual patient model according to the current step of the surgical plan, such as automatically based on objects and surfaces detected by the computer system in the surgical field or responsive to explicit input from the surgeon.

13. Post-Resection: Registration

Blocks S150, S156, and S154 of the method S100 recite, during a second period of time succeeding resection of the hard tissue of interest within the surgical operation: accessing a second sequence of optical scans recorded by the optical sensor; detecting the set of intermediate features in the second sequence of optical scans; and registering the virtual patient model to the hard tissue of interest based on the spatial relationship and the set of intermediate features detected in the second sequence of optical scans.

Generally, during the surgical operation, the surgeon may reorient, relocate, and/or modify a contour (or "surface," "surface profile") of the hard tissue of interest or other anatomical component within the surgical field. In particular, visible features on the hard tissue of interest with which the computer system initially registered the virtual patient model to the patient's anatomy may change contour, dimensions, and/or be removed entirely during the surgical operation. Therefore, the computer system can implement Blocks S156 and S154 to preserve registration of the virtual patient model to the patient's anatomy via nearby intermediate features—such as soft tissue, the mechanical axis of the hard tissue of interest, and/or features on the hard tissue of interest but offset from the resected contour on the hard tissue of interest—that have not substantively changed following resection of the hard tissue of interest (such as other than deformation of soft tissue due to movement, gravity, and other applied strains, such as surgical tools placed on the patient).

In one implementation, the computer system tracks actual 3D contours of exposed hard tissues in a subsequent sequence of optical scans and compares these 3D contours to virtual unresected contours of the corresponding tissues of interest defined in the virtual patient model. When the computer system detects a difference between the actual 3D contour of an exposed hard tissue in the surgical field and the virtual unresected contours of the corresponding hard tissue of interest defined in the virtual patient model, the computer system can transition to registering the virtual patient model to the patient based on positions of the intermediate features detected in the surgical field and the stored spatial relationship between these intermediate features and the virtual patient model.

Once the intermediate features are selected by the computer system, the computer system can continue to track these intermediate features in the surgical field, such as by implementing 3D object tracking to track these intermediate features in subsequent optical scans, and then locate the virtual patient model relative to these intermediate features based on the stored spatial relationship for this hard tissue of interest. For example, during a particular scan cycle, the computer system can: record an optical scan; detect at least a subset of the intermediate features in the optical scan; calculate a 3D position of the intermediate origin for these detected intermediate features during this scan cycle; implement the stored spatial relationship between these intermediate features and the virtual patient model for this hard tissue of interest to calculate a model origin of the virtual patient model relative to these intermediate features; and then project the virtual patient model onto this model origin, thereby registering the virtual patient model to the patient's hard tissue of interest via these intermediate features (e.g., soft tissue features). The computer system can repeat this process throughout the surgery to preserve registration of the virtual patient model to the patient's hard tissue of interest, as shown in FIG. 1B.

Therefore, the computer system can: track visible skin features—such as in addition to other features in the constellation of intermediate features defined in Block S140—in a sequence of optical scans following resection of the hard tissue of interest; and then regularly realign the virtual patient model to the hard tissue of interest based on three-dimensional positions of visible skin features detected in optical scans of the surgical field and based on the stored spatial relationship between the virtual patient model and these visible skin features.

13.1 Soft Tissue Deformation

In one variation, the computer system implements a gravity-based model for soft tissue (e.g., skin, muscle) to predict deformation of soft tissue features contained in the set of intermediate features based on changes in position and orientation of the patient during the surgical operation (e.g., the patient's upper and lower leg during a total knee replacement surgery). In particular, in this variation, the computer system can: detect an orientation of the hard tissue of interest relative to gravity; deform the constellation of soft tissue features (e.g., visible skin features)—in the set of intermediate features—according to a soft tissue gravity model based on the orientation of the hard tissue of interest relative to gravity; and then apply the stored spatial relationship between these intermediate features to the virtual patient model to register the virtual patient model to the patient via this deformed constellation of intermediate tissue features.

For example, the virtual patient model can include a soft tissue layer that represents the patient's skin and muscle tissue around the hard tissue of interest, as described below; and the computer system can populate or annotate this soft tissue layer of the virtual patient model with soft tissue features contained in the set of intermediate features. During the surgery, the computer system can: track the position and orientation of the hard tissue of interest in the surgical field; implement the gravity-based model for soft tissue to deform the soft tissue layer—including representation of the intermediate features—in the virtual patient model according to the position and orientation of the hard tissue of interest relative to gravity; extract a revised spatial relationship between virtual representations of these intermediate features and the hard tissue of interest in the virtual patient model; and then register the virtual representation of the hard tissue of interest in the virtual patient model to the real hard tissue of interest based on this revised spatial relationship.

In this variation, the computer system can implement a fixed gravity-based soft tissue deformation model. Alternatively, the computer system can generate a custom soft tissue deformation model to predict deformation of soft tissue around the hard tissue of interest as a function of position and orientation relative to gravity, such as based on changes in 3D skin surface geometry of the patient's soft tissue detected in a sequence of optical scans recorded by the optical sensor before, during, and after incision of the knee and prior to resection of the hard tissue of interest.

Therefore, the computer system can predict changes in spatial relationships between soft tissue features—in the constellation of intermediate features—relative to the hard tissue of interest as a function of position and orientation of the hard tissue of interest. The computer system can then implement these gravity-corrected spatial relationships to preserve registration of the virtual hard tissue of interest defined in the virtual patient model to the patient's real hard tissue of interest throughout the surgical operation.

14. Spatial Differences

Block S152 of the method S100 recites, during the second period of time succeeding resection of the hard tissue of interest within the surgical operation, detecting a second contour of the hard tissue of interest in the second sequence of optical scans; and Block S160 of the method S100 recites detecting a spatial difference between virtual hard tissue features defined in the virtual patient model and the resected contour of the hard tissue of interest detected in the second sequence of optical scans. Generally, in Blocks S152 and S160, the computer system can detect a change in the hard tissue of interest in the surgical field (e.g., resection of the hard tissue of interest) and compare this change to a virtual representation of the unresected contour defined in the virtual patient model—and registered to the patient via the set of intermediate features—in order to calculate quantitative metrics and/or geometric parameters describing the change in the hard tissue of interest from its original geometry, as shown in FIGS. 1B, 2, and 3. By then presenting these quantitative metrics and/or geometric parameters, the computer system can enable the surgeon to quickly ascertain the absolute magnitude and geometry of a change in the hard tissue of interest from its original state.

14.1 Absolute Resection Characteristics

In one implementation, the computer system implements methods and techniques described above (e.g., 3D object tracking) to track the hard tissue of interest in optical scans of the surgical field throughout the surgery. For each optical scan (or set of optical scans), the computer system can also: extract a 3D surface profile of the hard tissue of interest from the optical scan; register the virtual patient model to the patient via the constellation of intermediate features; and then calculate a 3D volumetric disjoint between the virtual unresected contour of the hard tissue of interest defined in the virtual patient model and the 3D surface profile of the hard tissue of interest derived from the optical scan. The computer system can then characterize this 3D volumetric disjoint, such as by: storing a maximum thickness of the 3D volumetric disjoint as a resection magnitude for the hard tissue of interest; calculating an orientation of a longitudinal axis of the 3D volumetric disjoint relative to a longitudinal axis or primary axis of the hard tissue of interest; or characterizing a flatness of concentricity, etc. of a resected contour represented by the 3D volumetric disjoint; etc.

In one example in which the virtual patient model defines a femur as a hard tissue of interest, the computer system can: detect a femoral condyle in an optical scan; extract the actual resected surface of the femoral condyle from the optical scan, such as in the form of a virtual 3D contour or surface flow of the resected surface of the femoral condyle; and detect a spatial difference between virtual unresected femoral condyle features defined in the virtual patient model—aligned to the patient via the set of intermediate features—and this virtual representation of the actual resected surface of the femoral condyle extracted from the optical scan. In particular, in this example, the computer system can: calculate a magnitude of resection of the femoral condyle based on the spatial difference; calculate an orientation of the resected surface of the femoral condyle based on the spatial difference; and/or characterize a surface profile or form of the resected contour of the femoral condyle, such as concentricity, flatness, angularity, symmetry, or position relative to a reference on the femur (e.g., the mechanical axis of the femur).

In this example, the virtual patient model can define a tibia as a second hard tissue of interest. The computer system can therefore: detect a tibial plateau in the same or other optical scan; extract the actual resected surface of the tibial plateau from the optical scan; and detect a spatial difference between virtual unresected tibial plateau features defined in the virtual patient model—aligned to the patient via the set of intermediate features—and this virtual representation of the actual resected surface of the tibial plateau extracted from the optical scan. In particular, in this example, the computer system can: calculate a magnitude of resection of the tibial plateau based on the spatial difference; calculate an orientation of the resected surface of the tibial plateau based on the spatial difference; and/or characterize a surface profile or form of the resected contour of the tibial plateau, such as concentricity, flatness, angularity, symmetry, or position relative to a reference on the femur (e.g., the mechanical axis of the femur).

In this implementation, the computer system can then visually indicate to the surgeon this absolute difference between the original state of the hard tissue of interest and the resected contour of the hard tissue of interest, such as by serving the magnitude of resection, the orientation of resection, and the surface profile to the surgeon. For example, the computer system can implement methods and techniques described above and below to: generate an augmented reality frame depicting the virtual unresected contour of the hard tissue of interest aligned to the actual hard tissue of interest—now resected—in the surgeon's field of view of the surgical field; and serve this augmented reality frame to an augmented reality headset worn by the surgeon for rendering in near real-time. In this example, the computer system can: detect a position of an augmented reality headset—worn by a surgeon—proximal the surgical field; estimate a perspective of the surgeon viewing the surgical field based on the position of the augmented reality headset in the surgical field; generate an augmented reality frame that includes a projection of the virtual unresected hard tissue of interest aligned with the real hard tissue of interest of the patient from the perspective of the surgeon; insert the magnitude of resection, the orientation of resection, and the surface profile of the hard tissue of interest—derived from the last optical scan of the surgical field—into an augmented reality frame; and then serve this augmented reality frame to the augmented reality headset. The augmented reality headset can then render the augmented reality frame in near real-time.

14.2 Deviation from Target Resection

The computer system can additionally or alternatively compare the actual resected contour of the hard tissue of interest thus detected in the surgical field to the target resected contour of the hard tissue of interest defined in the virtual patient model in order to calculate quantitative metrics and/or geometric parameters describing a difference between the actual and target resected contours of the hard tissue of interest. By then presenting this difference to the surgeon, the computer system can enable the surgeon to quickly ascertain both whether the surgeon has deviated from the surgical plan and a magnitude of this deviation, such as in six degrees of freedom.

In one implementation shown in FIG. 2, the computer system: extracts an actual resection contour of the hard tissue of interest of the patient from an optical scan, as described above; and calculates a spatial difference between the actual resected contour of the hard tissue of interest and the target resected contour defined in the virtual patient model. For example, the computer system can: calculate a distance magnitude difference between the actual resected contour of a femoral condyle and the target resected contour of a femoral condyle defined in the virtual patient model, such as in the form of a maximum distance in millimeters between the actual and target resected contours of the femoral condyle normal to the target resected contour or parallel to the mechanical axis of the femur. The computer system can additionally or alternatively calculate an orientation difference between the actual resected contour of the femoral condyle and the target resected contour of the femoral condyle, such as by calculating a best-fit plane of the actual resected contour of the femoral condyle; and calculating angular offsets between a target resect plane of the femoral condyle defined by the virtual patient model and the actual resected contour of the femoral condyle extracted from the optical scan. The computer system can also characterize a surface profile difference between the actual resected contour of the femoral condyle and the target resected contour of the femoral condyle, such as differences between actual and target surface roughness, texture, flatness, and/or symmetry, etc. of the femoral condyle. The computer system can then present these distance magnitude difference, orientation difference, and surface profile difference metrics to the surgeon, such as via an augmented reality headset worn by the surgeon or via a display present near the surgical field.

14.3 Surgical Implant

Furthermore, once the surgeon has resected each hard tissue of interest to within a specified tolerance or verified a deviation from the surgical plan, the surgeon may then locate one or more surgical implants on the tissue(s) of interest. The computer system can then implement methods and techniques similar to those described above to: detect and track a surgical implant in the surgical field; calculate an actual position of the surgical implant relative to its corresponding hard tissue of interest; calculate a spatial difference between the actual position of the surgical implant relative to the hard tissue of interest and a target position of the surgical implant relative to the hard tissue of interest as defined in the virtual patient model (or otherwise defined in a surgical plan for the surgery); and then communicate this spatial difference to the surgeon, such as via augmented reality frames served to the surgeon's augmented reality headset, as shown in FIG. 3.

For example, during the surgery the surgeon may place an artificial femoral component over the patient's resected femoral condyle. In this example, the virtual patient model can include a layer defining a target position of a femoral component relative to the hard tissue of interest. The computer system can therefore implement methods and techniques described herein and in U.S. patent application Ser. No. 15/594,623 to generate an augmented reality frame depicting the target location of the femoral component aligned to the hard tissue of interest in the surgeon's field of view of the surgical field. An augmented reality headset worn by the surgeon can then render this augmented reality frame in order to visually guide the surgeon in aligning the femoral component to its target position on the patient's femur. Similarly, the computer system can implement methods and techniques described below to detect a difference between the actual and target positions of the femoral component on the femur and can then prompt the user to make adjustments to the position of the femoral component accordingly prior to fastening or bonding the femoral component to the resected femoral condyle.

For example, the computer system can: access a sequence of optical scans recorded by the optical sensor after the surgeon confirms resection of the tissue(s) of interest; detect the set of intermediate features in this sequence of optical scans; register the virtual patient model to the hard tissue of interest based on the stored spatial relationship linking the set of intermediate features to the virtual patient model; and detect the surgical implant in the sequence of optical scans, such as by implementing template matching or object recognition techniques to match features extracted from the optical scans to a virtual surgical implant model contained in the virtual patient model or otherwise linked to the surgery. The computer system can then: calculate an actual position of the surgical implant relative to the virtual patient model registered to the hard tissue of interest based on the spatial relationship and the set of intermediate features; and calculate a spatial difference between the actual position of the surgical implant and the target position of the surgical implant relative to the hard tissue of interest accordingly. The computer system can then render this spatial difference on a display near the surgical field or serve an augmented reality indicating this spatial difference to the surgeon's augmented reality headset, thereby: guiding the surgeon in aligning the surgical implant to the target implant location specified in the surgical plan; and/or enabling the surgeon to intentionally deviate from this surgical plan by an indicated quantitative linear distance and/or angular offset.

The computer system can repeat this process for each other surgical implant designated for the surgery.

14.4 Cumulative Deviation

In one variation, the computer system can track (or log) each deviation from the surgical plan throughout the surgery, such as differences between actual and target resected contours of tissues of interest and/or differences between actual and target surgical implant positions relative to corresponding tissues of interest. At each step of the surgical operation, the computer system can then calculate a current cumulative deviation (or "error") throughout the surgery up to the current step of the surgical plan. The computer system can then present this cumulative deviation to the surgeon (e.g., via an eyes-up or heads-up display in an AR headset worn by a surgeon) throughout the surgery.

For example, during a total knee replacement surgery, the computer system can: predict how a difference between the actual and target resected contours of the patient's femoral condyle will result in a difference between the actual and target positions of an artificial femoral component on the patient's femur when later installed during the surgery based on the actual geometry of the resected femoral condyle and a known geometry of the artificial femoral component; and then present this predicted deviation to the surgeon in order to quantitatively communicate to the surgeon how the result of this current step may affect a future step of the surgery. As the surgeon transitions to resecting the patient's tibial plateau, the computer system can similarly: predict how a difference between the actual and target resected contours of the patient's tibial plateau will result in a difference between the actual and target positions of an artificial tibial component on the patient's tibia when later installed during the surgery based on the actual geometry of the resected tibial plateau and a known geometry of the artificial tibial component; and then present this predicted deviation to the surgeon. The computer system can further combine these femoral and tibial deviations to predict a cumulative deviation at conclusion of the surgery, such as including: a spatial difference between the pre-operative and post-operative joint centers of rotation of the patient's knee; a difference between the pre-operative and post-operative lengths of the user's leg; a difference between the pre-operative and post-operative angular resting position of the patient's foot relative to the patient's hip; and/or a difference between the patient's pre-operative and post-operative gait; etc. The computer system can then present these predicted deviations to the surgeon in real-time, thereby enabling the surgeon to better comprehend, mitigate, and/or verify such deviations from the surgical that may occur upon conclusion of the surgery.

The computer system can continue to generate and serve such deviation predictions to the surgeon as the surgeon refines resected contours on the tissues of interest, places surgical implants on the tissues of interest, and fastens these surgical implants onto their corresponding tissues of interest.

In another implementation, during the surgery, the computer system can log deviations during the surgery in memory and project these prior deviations onto the field of view of the surgeon—aligned with the hard tissue of interest within the surgical field—during surgery. Therefore, the surgeon may, in real-time, play back prior deviations and visualize their cumulative effects on the patient's anatomy at present to inform imminent placement of implants and/or upcoming surgical steps. For example, the computer system can render a frame—projected onto the field of view of the surgeon—representing a last cut across a femur performed by the surgeon aligned with the hard tissue of interest in the surgical field. The computer system can also insert an image of the hard tissue of interest prior to the last cut, an outline of the hard tissue of interest after the last cut, and a virtual guide for a next cut into the frame.

14.5 Deviation Notes and Storage

In one variation shown in FIG. 3, the computer system also interfaces with the surgeon to verify intent to deviate from the surgical plan—such as intent to deviate from a target resected contour of a hard tissue of interest, intent to deviate from a target position of a surgical implant relative to the hard tissue of interest, and/or intent to deviate from target relative positions of two adjacent surgical implants—and to record these deviations from the surgical plans, confirmation of the surgeon's intent to deviate, and the surgeon's reasons for these deviations.

In one implementation, after detecting a spatial difference between an actual and a target resected contour of the hard tissue of interest, the computer system prompts the surgeon to confirm her intent to deviate from the surgical plan according to the spatial difference. In response to confirmation of intent to deviate from the surgical plan according to the spatial difference, the computer system can also prompt the surgeon to provide a reason for this deviation. The computer system can then record a reason spoken orally by the surgeon in real-time during the surgery or record a text-based response provided by the surgeon (or nurse or other staff nearby) via the user interface. Upon receipt of this reason, the computer system can store: a representation of the spatial difference (e.g., in the form of a 3D virtual contour of the resected hard tissue of interest extracted from a recent optical scan); confirmation of the surgeon's intent to deviate from the surgical plan according to the spatial difference; and the reason for the deviation provided by the surgeon, such as in a database or in a surgery file associated with the patient and surgical operation. In this implementation, the computer system can also gate a next step of the surgery (or guidance for a next step of the surgery) until the surgeon either: confirms her intent to deviate from the surgical plan and provides a reason for the deviation; or requests guidance to return to the surgical plan.

Alternatively, the computer system can store the representation of the spatial difference and confirmation of the surgeon's intent to deviate from the surgical plan during the surgery. Upon conclusion of the surgery, the computer system can retroactively prompt the surgeon to provide a reason for the deviation (e.g., in post-operative surgery notes). For example, the computer system can present the representation of the spatial difference between the target and actual resected contours of the hard tissue of interest to the surgeon via a physician portal and prompt the surgeon to annotate the representation with a reason for the deviation.

The computer system can implement similar methods and techniques to store representations, intents, and reasons for deviations from target resected contours of other tissues of interest, target placement of surgical implants relative to these tissues of interest, and/or target relative positions of two surgical implants located in the patient during the surgery.

However, in this variation, if the surgeon requests guidance to return to the surgical plan, the computer system can implement methods and techniques described below to guide the surgeon in refining the resected contour to correct the deviation, as described below.

14.6 Remote Guidance

Alternatively, in response to detecting such deviation from the surgical plan, the computer system can: generate virtual reality frames depicting both real tissue of interest in the surgical field and virtual content (e.g., target resected contours of tissues of interest defined in the virtual patient model thus registered to the real patient tissue); serve these virtual reality frames to a virtual reality headset worn by a remote surgeon logged into the surgery; and prompt the remote surgeon to suggest changes to the surgical plan. For example, the computer system can prompt the remote surgeon to: move virtual objects (e.g., virtual guides, virtual artificial components) or virtual surfaces (e.g., target resected contours) in these virtual frames in order to modify or redefine target parameters for this surgery; selectively authorizing next steps of the surgical plan; and communicating directly with the local surgeon—such as through an audio and/or video feed—to discuss and verify changes to the surgical plan.

The computer system can therefore detect deviation from the surgical plan and automatically prompt a remote surgeon to assist the local surgeon in real-time during the surgery when such deviations are detected.

15. Adaptation and Guidance

In one variation shown in FIG. 2, in response to detecting deviation between an actual resected contour of the hard tissue of interest extracted from an optical scan and a target resected contour defined in the virtual patient model, the computer system can: modify subsequent steps of the surgical plan to account for, adapt to, and/or negate deviations between actual and target resected contours of the hard tissue of interest; and can update layers of the virtual patient model to virtually reflect these modifications.

In one implementation, the computer system modifies a subsequent step of the surgical plan to correct or counteract a detected deviation. In this implementation, the computer system can detect a deviation from the surgical plan that affects a reference point, a reference angle, a reference plane, etc. from which a datum in a subsequent step is referenced. Therefore, the computer system can modify the particular subsequent step of the surgical plan to reference a datum defined by a different feature, incision, etc.

Figure 5:
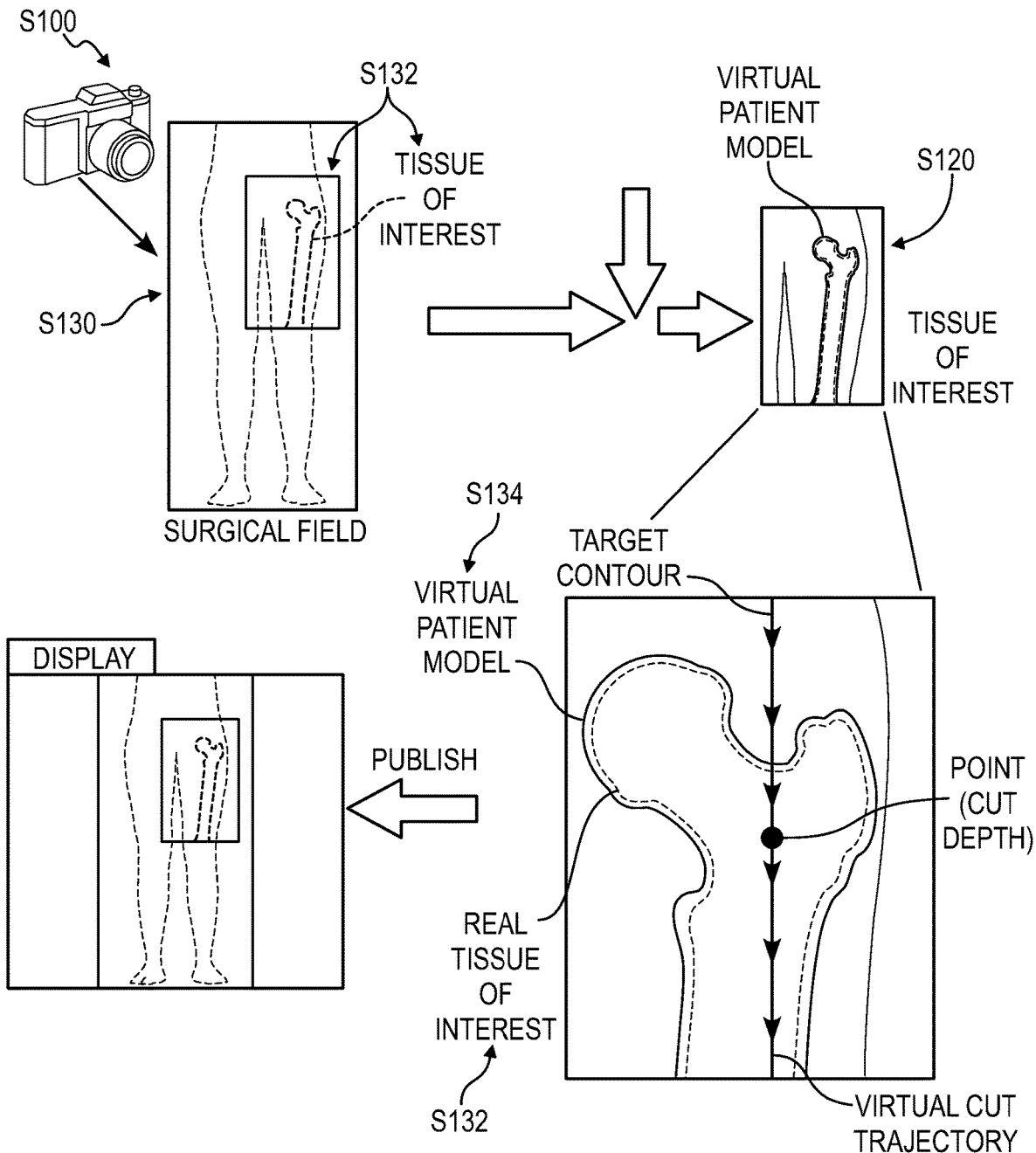
FIG. 5 is a flowchart representation of one variation of the method.

Alternatively, the computer system can modify another target resected surface of one hard tissue of interest (e.g., a tibial plateau) based on the actual resected contour of a nearby hard tissue of interest (e.g., a femoral condyle). For example and as shown in FIG. 5, the computer system can access a surgical plan for a hip replacement surgery that defines: a first surgical step transecting a femoral head of a femur along a target cut plane; and a second surgical step boring into the femur along a mechanical axis (i.e., load bearing axis through the femur parallel direction of gravity) of the femur, a bore of the second surgical step at an angle to the target cut plane of the first surgical step. In this example, the computer system can detect a deviation in the first surgical step in which a real cut plane resulting from completion of the first surgical step in the surgical field is offset from (or skew to) the target cut plane by three degrees. Because the bore of the second surgical step is defined relative to the target cut plane of the first surgical step, the computer system can adjust the second surgical step to locate the bore at a new angle (e.g., smaller angle) relative to the real cut plane executed in the first surgical step such that the bore aligns with the mechanical axis of the femur despite the deviation in the first surgical step.

In the foregoing example, the computer system can additionally or alternatively define an intermediate step—between the first surgical step and the second surgical step—that specifies a re-planing operation to cut the femoral head parallel to the (former) target cut plane defining the first surgical step in order to correct the offset (or "skew") that resulted during the first surgical step. Following completion of the intermediate step, the computer system can detect a deviation of one centimeter between the target cut plane of the first surgical step and an actual cut plane of the femoral head resulting from the re-planing operation defined in the intermediate step.

In another example, after detecting a deviation between an actual resected contour of the hard tissue of interest and a target resected contour extracted from a first surgical step of a surgical plan (and receiving confirmation of intent of this deviation from the surgeon), the computer system can determine that the deviation directly affects no other subsequent step of the surgical plan. Therefore, the computer system can record the deviation as described above and notify the surgeon of acceptance of the deviation.

Similarly, the computer system can cooperate with a surgeon to modify subsequent steps of the surgical plan. The computer system can serve a prompt to the surgeon to communicate the deviation, a predicted effect of the deviation on subsequent surgical steps and/or surgical outcome, and a suggested modification to a subsequent step that may correct this deviation or lessen compounding effects of this deviation.

However, the computer system can modify, maintain, add, and/or remove any subsequent steps of the surgical plan to adapt to deviations and limit problems in subsequent steps of the surgery in any other suitable way, such as independently and/or in cooperation with the surgeon.

15.1 Insufficient Resection

In a similar variation shown in FIG. 1B, the computer system prompts the user to refine a resected contour on a hard tissue of interest in response to detecting insufficient material removal from the hard tissue of interest based on the spatial difference. For example, the computer system can extract a 3D contour of the exposed hard tissue of interest in the surgical field following resection by the surgeon and compare this 3D contour of the actual resected hard tissue of interest to the target resected contour of the hard tissue of interest defined in the virtual patient model in order to determine whether any portion of the actual resected surface of the hard tissue of interest extends beyond (i.e., falls outside of) the target resected contour of the hard tissue of interest defined. More specifically, the computer system can determine whether insufficient material has been removed from any portion of the hard tissue of interest as defined in the surgical plan. If the computer system thus detects that a portion of the resected surface of the hard tissue of interest still extends beyond the target resected contour of the hard tissue of interest, such as beyond a threshold offset or maximum tolerance, then the computer system can serve a prompt to the surgeon to remove additional material from this region of the hard tissue of interest. For example, the computer system can highlight—via the augmented reality headset worn by the surgeon—portions of the hard tissue of interest that extend beyond the target contour of the hard tissue of interest defined in the virtual patient model.

The computer system can then repeat the foregoing methods and techniques to monitor this surface of the hard tissue of interest and to calculate a second spatial difference between the actual resected contour of the hard tissue of interest detected in a next sequence of optical scans and the target resected contour of the hard tissue of interest represented in the virtual patient model—which is still registered to the hard tissue of interest. The computer system can then: confirm that the actual resected contour falls within a predefined tolerance of the target resected contour (e.g., by rendering confirmation on the surgeon's augmented reality headset); prompt the surgeon to further resect the hard tissue of interest if insufficient material has been removed from the hard tissue of interest; or respond to excessive removal of material from the hard tissue of interest by modifying a later step of the surgery, as described below.

15.2 Excessive Resection

In a similar variation shown in FIG. 1B, the computer system modifies a target resected contour for a second hard tissue of interest (e.g., a tibial plateau)—such as automatically or with guidance from the surgeon—responsive to detecting excessive material removal from a first hard tissue of interest (e.g., a femoral condyle) based on the spatial difference calculated in Block S160. For example and as described above, the computer system can extract a 3D contour of the exposed femoral condyle in the surgical field following resection by the surgeon and compare this 3D contour of the actual resected femoral condyle to the target resected contour of the femoral condyle defined in the virtual patient model to determine whether any portion of the target resected contour of the femoral condyle defined in the virtual patient model extends beyond (i.e., falls outside of) the actual resected surface of the femoral condyle—that is, if excessive material has been removed from any portion of the femoral condyle beyond resection defined in the surgical plan. If the computer system thus detects that a portion of the resected surface of the femoral condyle has been removed beyond the target resected contour defined in the virtual patient model—such as beyond a threshold offset or maximum tolerance defined in the surgical plan—the computer system can: calculate a best fit plane (or other mating profile defined by an artificial femoral component) of the resected contour; calculate a direction and orientation of the offset between this best fit plane (or other mating profile) and the target resected contour of the femoral condyle; and offset a target resected contour of the adjacent tibial plateau opposite this direction and orientation of the femoral condyle offset. (The computer system can similarly modify the target resected contour of the adjacent tibial plateau to compensate for this femoral condyle offset based on a known interaction between the artificial femoral component and an artificial tibial component specified for the surgery). In this example, responsive to removal of excessive material from the patient's femoral condyle, the computer system can: automatically shift the target resected contour of the patient's tibial plateau to compensate; and/or predict a thicker shim between artificial femoral and tibial components installed on the patient during later steps of the surgery.

In this variation, the computer system can also prompt the surgeon to confirm or adjust this modification to the target contour of the tibial plateau before updating the virtual patient model accordingly.

In this example, the computer system can repeat the foregoing processes once the tibial plateau is resected to calculate an offset between the actual and (modified) target resected contours of the tibial plateau. Accordingly, the computer system can: predict a shim thickness and/or wedge geometry that compensates for both spatial differences between actual and target resected contours of the femoral condyle and tibial plateau; and serve this prediction to the surgeon, such as to inform the surgeon of predicted effects of the current states of these tissues of interest.

15.3 Outcome Probability

In another variation shown in FIG. 1B, the computer system leverages a patient outcome model—linking absolute and/or relative resected tissue contours and/or surgical implant positions for a surgery type to patient recovery, recovery rate, satisfaction, etc.—to predict longer-term effects of tissue resection and/or surgical implant placement during the surgery on the patient.

In one implementation, the computer system: calculates an absolute spatial difference between the actual resected contour of the hard tissue of interest detected in an optical scan and an unresected contour of the hard tissue of interest defined in the virtual patient model, as described above; accesses a correlation between outcomes and absolute spatial differences between actual resected contours of the hard tissue of interest and unresected contours of the hard tissue of interest within a population of patients subject to instances of the surgical operation, such as defined in the patient outcome model; and predict a probability of successful outcome of the patient (e.g., probability that the patient will regain 95% of her range of motion; probability that the patient will fully recover within six months of the surgery; low probability of infection; low probability of a second corrective surgery; high probability of patient satisfaction) based on the absolute spatial difference and the patient outcome model. Then, if the computer system predicts a high probability of successful outcome (e.g., a probability of successful outcome that exceeds a threshold probability) given the current resected state of one or more tissues of interest in the surgical field, the computer system can prompt the surgeon to move to a next step of the surgical operation. However, if the computer system predicts a low probability of successful outcome given the current resected state of one or more tissues of interest in the surgical field, the computer system can prompt the surgeon to correct the actual resected contour of the hard tissue of interest, such as according to methods and techniques described above to reduce the spatial difference.

The computer system can implement similar methods and techniques to predict probability of a successful outcome for the patient based on absolute resection of a hard tissue of interest—such as relative to an original state of the hard tissue of interest relative to the mechanical axis of the hard tissue of interest—rather than based on a difference between the target and actual resected contours of the hard tissue of interest.

Furthermore, as the surgeon resects various tissues of interest, refines these resected contours, and completes each subsequent step of the surgery, the computer system can input absolute or relative spatial differences between actual and target resected contours for these tissues of interest in order to: update the predicted probability of successful outcome for the surgery; and thus inform changes to a subsequent step of the surgery or prompt refinement of a current step of the surgery.

Furthermore, the computer system can implement similar methods and techniques to predict probability of successful outcome for the surgery based on the absolute or relative positions of surgical implants placed on corresponding tissues of interest during the surgery. For example, after the patient's femoral condyles and tibial plateau are resected by the surgeon, the surgeon may place an artificial femoral component over the resected end of the patient's femur. The computer system can then: calculate an absolute position of the artificial femoral component over the resected femoral condyle detected in an optical scan; access a correlation between outcomes and absolute positions of instances of a artificial femoral component on resected femoral condyles within a population of patients subject to total knee replacement surgeries; and predict a probability of successful outcome of the patient based the absolute position of the artificial femoral component on the patient's resected femoral condyle. In response to the probability of successful outcome exceeding a threshold probability, the computer system can prompt the surgeon to fasten the artificial femoral component to the patient's femur in its current position and/or move to a next step of the surgical operation. However, in response to the probability of successful outcome falling below the threshold probability, the computer system can prompt the surgeon to adjust the absolute position of the artificial implant on the hard tissue of interest; as the surgeon adjusts the position of the artificial femoral component, the computer system can track the position of the artificial femoral component relative to the hard tissue of interest (e.g., relative to the registered virtual patient model) and recalculate the probability of successful outcome for the patient accordingly.

16. Prediction

In one variation, the computer system can access historical surgical data (e.g., instances of the virtual representation, records of surgeries, deviations from surgical plans, and/or compliance with surgical plans) to extract trends in deviations from surgical plans for particular surgeons, particular surgical steps, and/or particular surgery types. Based on these trends, the computer system can predict times, locations, magnitudes, and types of deviations to surgical plans for future operations and adapt the surgical plans accordingly.

In one implementation, the computer system can access historical surgical data (e.g., recorded over a one-month period, over a two-year period, and/or over the entire career of a particular surgeon) from a remote computer system documenting surgeries performed by a particular surgeon. From the historical data, the computer system can extract trends in the deviations from surgical plans the particular surgeon executes for particular surgical steps, surgery types, patient anatomy, patient demographics, etc. From these trends in deviations for the particular surgeon, the computer system can adapt surgical plans for all future surgeries scheduled to be performed by the surgeon to anticipate when the surgeon will deviate, the surgeon's preferred course of action following the deviation, etc.

For example, the computer system can extract a trend from historical surgical data for a particular surgeon indicating a surgeon consistently deviates five to ten millimeters from a prescribed target resected contour at a first surgical step in a surgical plan. The computer system can extract a tolerance range for cuts executed by the surgeon (e.g., between five and ten millimeters for the first surgical step). The computer system can then modify future surgical plans to accept deviations within the tolerance range for the particular surgeon and guide the surgeon to remain within the tolerance range throughout surgery. Additionally or alternatively, the computer system can calculate a cumulative tolerance stackup for the surgery defined as a sum of a maximum predicted deviation for all or a subset of steps of the surgery based on the tolerance range for cuts executed by the surgeon. The computer system can then define an acceptable tolerance window for each surgical step within which the computer system can accept deviations without updating subsequent steps and guide the surgeon to remain within the acceptable tolerance window.

In another example, the computer system can extract a trend from historical surgical data for a particular surgeon indicating a surgeon routinely elects (i.e., intentionally) to drill into a femur with a drill-bit smaller than that which was recommended in the surgeon's surgical plans. The computer system can, therefore, modify future surgical plans to incorporate the small drill-bit and preemptively model effects (e.g., hole size of the incision by the small drill-bit, duration the small drill-bit is inserted to yield a target hole size, and/or trajectory of the small drill-bit) of drilling into a bone with the small drill-bit. Furthermore, the computer system can calculate effects of drilling into a bone with the small drill-bit on subsequent steps of the surgical plan and adapt the subsequent steps accordingly. For example, the computer system can add additional steps of boring out the hole with two distinct bores to form a hole of a size sufficient to accept an artificial hip implant.

In another example, the computer system can extract a trend from historical surgical data for a particular surgeon indicating a surgeon routinely elects (i.e., intentionally) to ream and broach a femur at a slight angle to a mechanical axis of the femur instead of executing a planned (target) ream into the femur aligned with the mechanical axis as defined in the surgical plan. Based on consistent election of the ream at a slight angle to the mechanical axis, the computer system can anticipate the surgeon will elect to execute similar broaches into the femur at the slight angle to the mechanical axis. Therefore, the computer system can adapt the surgeon's surgical plan for hip replacement surgeries to preemptively define the broach at the slight angle to the mechanical axis. Additionally, the computer system can preemptively adapt subsequent steps of the hip replacement surgical plan to account for a ream and broach at the slight angle to the mechanical axis. For example, based on the slight angle, the computer system can virtually model a position of an artificial hip implant following implantation into the femur; from the position of the artificial hip implant, the computer system can predict the position and angle of a transecting cut across the femoral head (i.e., a step preceding the bore into the femur).

In another example, the computer system can detect a particular surgeon prefers to cut a tibia one degree varus for patients of a first demographic group (e.g., sedentary females) and one degree valgus for patients of a second demographic group (e.g., active males) based on historical surgical data for the particular surgeon. Therefore, the computer system can define a first surgical plan for the first demographic group to include a one-degree varus target resected contour; additionally, the computer system can calculate a one-degree rotation of the tibia resulting from the one-degree varus target resected contour and adapt subsequent steps of the first surgical plan accordingly. Similarly, the computer system can define a second surgical plan for the second demographic group to include a one-degree valgus target resected contour. The computer system can also calculate a one-degree rotation of the tibia resulting from the one degree valgus target resected contour and adapt subsequent steps of the second surgical plan accordingly.

Similarly, the computer system can access historical surgical data (e.g., recorded over a one-month period, over a two-year period, over a ten-year period, and/or indefinitely) from a remote computer system documenting surgeries of a particular type (e.g., knee replacement surgery) performed by a group of surgeons. From the historical data, the computer system can extract trends in the deviations from surgical plans the group of surgeons execute for surgeries of a particular type. From these trends in deviations for the particular surgeon, the computer system can adapt surgical plans for all future surgeries scheduled to be performed by each surgeon in the group of surgeons to anticipate when the surgeons will deviate from the surgical plans and preemptively adapt the surgical plans to accommodate preferences of the group of surgeons for each step of the surgical plans.

However, the computer system can apply historical surgical deviation data to inform surgical plan definitions in any other suitable way.

17. Deviation and Patient Outcome Model

Furthermore, by tracking and recording deviations as described above, the computer system can correlate surgical deviations with patient outcomes (e.g., restoration of range of motion, reduction of pain levels, improved levels of function and/or mobility, increase in activity level, and/or high patient satisfaction scores) to inform future surgical practices and surgical plans. In particular, the computer system can maintain a record of actual resected contour of the tissues of interest, surgical deviations, and surgical outcomes for a plurality of surgeries; extract trends from the historical surgical data; and apply these trends to inform surgical plans, outcomes, and acceptable deviations for future surgeries.

In one implementation, the computer system can access patient outcome data from a remote database. In this implementation, patients and/or medical staff may manually enter into the remote database (i.e., through a user portal rendered on a display of a computing device) patient outcome data, such as pain levels, patient satisfaction surveys, levels of mobility, activity level, etc. Alternatively, a patient's computing device (e.g., smartphone) can automatically upload (or push) patient activity data (e.g., pedometer readouts, heartrate, etc.) to the remote database, such as over a wireless network.

For example, the computer system can detect that a particular surgeon routinely cuts femurs one degree varus and patients of the particular surgeon typically exhibit poor outcomes (e.g., high pain levels, limited range of motion, and/or low recorded activity levels post-surgery). Therefore, the computer system can modify surgical plans for the particular surgeon with additional or more detailed virtual guides to guide the surgeon to avoid cutting femurs one degree varus. Additionally, the computer system can adapt (or populate) surgical plans to guide other surgeons to avoid cutting femurs one degree varus.

Similarly, the computer system can detect that patients of a particular surgeon routinely exhibit positive outcomes (e.g., low pain levels, restoration of range of motion, and/or success during physical therapy). The computer system can then extract trends in the particular surgeon's surgical plans and deviations to deduce resected contours, surgical steps, and tolerance windows that contribute to these positive outcomes. From these trends, the computer system can adapt future surgical plans for the particular surgeon and surgical plans for other surgeons to include these resected contours, surgical steps, and tolerance windows that contribute to the positive outcomes.

Thus, the computer system can correlate surgical outcomes with particular steps, resected contours, deviations, processes, etc. to inform development of improved surgical plans for each particular surgeon and for groups of surgeons.

However, the computer system can extract trends from historical surgical data and surgical outcomes to inform future surgical plans in any other suitable way.

17.1 Modeling

In one variation, the computer system aggregates surgical and patient outcome data and implements machine learning or statistical techniques to derive a relationship between patient outcomes and various features of these patients' surgeries.

In one implementation, the system aggregates surgical input data including: surgical plans for a population of patients on which a particular type of surgery (e.g., total knee replacements) were performed, such as defining target resected contours of tissues of interest and target surgical implant positions; actual resected contours of these tissues of interest and actual surgical implant positions detected during these surgeries; numbers of resected contour adjustments; surgical implant types, sizes, and geometries; etc. In this implementation, the computer system can also aggregate surgeon identifiers and patient demographics (e.g., age, gender, weight, pre-operative mobility, pre-operative fitness level, medical history) for surgeons and patients present in each of the surgeries. Furthermore, the computer system can aggregate patient outcome data for each of these surgeries, such as: range of motion regained by the patient, such as a function of time or at a target time (e.g., six months) post-surgery; whether the patient achieved a fully recover (e.g., within six months post-surgery); whether the patient experienced a post-operative probability of infection; whether a second corrective surgery was necessary; patient-reported satisfaction (e.g., from 0% to 100%); etc. for each surgery.

The computer system can then: assemble these surgical inputs, surgeons, and patient data types into one vector (or other data container) per patient in the population; label each vector with corresponding patient outcome data; and then implement deep learning, a convolutional neural network, regression, and/or other machine learning or statistical techniques to derive correlations between these surgical inputs and patient outcomes—corrected or adjusted for surgeon and patient demographic. The computer system can then store these correlations in a patient outcome model. Later, the computer system can: implement this patient outcome model to predict an outcome of a next surgery on a patient based on inter-operative surgical input data (e.g., resected contours, surgical implant placement) collected during the surgery; and serve feedback or guidance to the surgeon to verify or modify resection of tissues of interest and/or placement of surgical implants, as described above.

Furthermore, the computer system can: collect surgical input data during this surgery; label these surgical input data with patient outcome data as these patient outcome data become available over time; append a corpus of surgical input data and patient outcome data across this population with these new surgical input data and patient outcome data; and retrain the patient outcome model accordingly.

For example, during a surgery, the computer system can implement methods and techniques described above to calculate an absolute spatial difference between the actual resected contour of the hard tissue of interest detected in the first sequence of optical scans and the unresected contour of the hard tissue of interest and then record these data in association with the patient and surgeon. Later, the computer system can: label this absolute spatial difference with a post-operative outcome of the patient (e.g., the patient's satisfaction, the patient's recover time); and store the absolute spatial difference in a database with a corpus of absolute spatial differences labeled with patient outcomes for a set of instances of the surgical operation within a population of patients. Finally, the computer system can: derive a correlation between outcomes and absolute spatial differences between actual resected contours of the hard tissue of interest and unresected contours of the hard tissue of interest within this population of patients; and store this correlation in a patient outcome model.

Similarly, the computer system can derive correlations between patient outcomes and: differences between actual and target resected contours; and/or differences between actual and target surgical implant positions. For example, the computer system can implement methods and techniques described above to detect and track a spatial difference between target and actual resected contours for a hard tissue of interest during a surgery. The computer system can then: store this spatial difference in a database with a corpus of spatial differences labeled with patient outcomes for a set of instances of this surgical operation across a population of patients; and then derive a correlation between successful recoveries of patients within this population, such as for all patients or specifically patients operated on by this same surgeon); and spatial differences between actual resected contours of the hard tissue of interest and target resected contours of the hard tissue of interest, such as specified in surgical plans defined by this same surgeon.

Furthermore, in this variation, the computer system can leverage this patient outcome model to assist a surgeon in defining a pre-operative surgical plan for a next patient. For example, as the surgeon develops a surgical plan for the next patient within a physician portal, the computer system can: inject target resected contour and surgical implant values specified by the surgeon into the patient outcome model to predict effects of these values on the patient's predicted outcome; and then serve a recommendation to the surgeon for adjustment of the pre-operative surgical plan accordingly.

The computer systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any computer readable media such as RAMs, ROMs, flash memory, EEPROMs, optical devices (CD or DVD), hard drives, floppy drives, or any device. The computer-executable component can be a processor but any dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for tracking and adapting to deviations from surgical plans comprising:
   accessing a virtual patient model defining a target resected contour of a hard tissue of interest;
   during a first period of time succeeding resection of the hard tissue of interest within a surgical operation:
      accessing a first sequence of optical scans recorded by an optical sensor facing a surgical field occupied by a patient;
      detecting a set of features representing the patient in the first sequence of optical scans;
      registering the virtual patient model to the hard tissue of interest in the surgical field based on the set of features; and
      detecting an actual resected contour of the hard tissue of interest in the first sequence of optical scans;
   calculating a spatial difference between the actual resected contour of the hard tissue of interest detected in the first sequence of optical scans and the target resected contour of the hard tissue of interest represented in the virtual patient model registered to the hard tissue of interest in the surgical field;
   presenting the spatial difference to a surgeon during the surgical operation;
   labeling the spatial difference with a post-operative outcome of the patient;
   storing the spatial difference in a database with a corpus of spatial differences labeled with patient outcomes for a set of instances of the surgical operation within a population of patients; and
   deriving a correlation between outcomes and spatial differences between actual resected contours of the hard tissue of interest and target resected contours of the hard tissue of interest within the population of patients.

2. The method of claim 1:
   further comprising, during an initial period of time preceding the first period of time and succeeding incision of the patient proximal the hard tissue of interest:
      accessing an initial sequence of optical scans recorded by the optical sensor;
      detecting an unresected contour of the hard tissue of interest in the initial sequence of optical scans; and
      registering virtual hard tissue features defined in the virtual patient model to the unresected contour of the hard tissue of interest; and
      detecting the set of features, on the patient and proximal the hard tissue of interest, in the initial sequence of optical scans;
   further comprising deriving a spatial relationship between the set of features and the virtual patient model based on registration of the virtual patient model to the hard tissue of interest; and
   wherein registering the virtual patient model to the hard tissue of interest in the surgical field based on the set of features during the first period of time comprises registering the virtual patient model to the hard tissue of interest based on the spatial relationship and the set of features detected in the first sequence of optical scans.

3. The method of claim 2, further comprising:
   calculating an absolute spatial difference between the actual resected contour of the hard tissue of interest detected in the first sequence of optical scans and the unresected contour of the hard tissue of interest;
   labeling the absolute spatial difference with a post-operative outcome of the patient;
   storing the absolute spatial difference with a second corpus of absolute spatial differences labeled with patient outcomes for the set of instances of the surgical operation within the population of patients; and
   deriving a second correlation between outcomes and absolute spatial differences between actual resected contours of the hard tissue of interest and unresected contours of the hard tissue of interest within the population of patients.

4. The method of claim 3:
wherein deriving the second correlation between outcomes and spatial differences comprises deriving the second correlation between:
successful recoveries within the population of patients; and
absolute spatial differences between actual resected contours of the hard tissue of interest and unresected contours of the hard tissue of interest within the population of patients; and
further comprising, for a second instance of the surgical operation planned for a second patient, generating a recommended absolute spatial difference between actual resected contours of the hard tissue of interest and unresected contours of the hard tissue of interest in the second patient, during the second instance of the surgical operation, based on the correlation.

5. The method of claim 2:
wherein accessing the virtual patient model comprises accessing the virtual patient model defining a virtual representation of a generic unresected contour of the hard tissue of interest and a virtual representation of a generic target resected contour of the hard tissue of interest;
wherein registering virtual hard tissue features defined in the virtual patient model to the unresected contour of the hard tissue of interest comprises:
calculating a best-fit location that minimizes error between the virtual representation of the generic unresected contour of the hard tissue of interest and the unresected contour of the hard tissue of interest detected in the initial sequence of optical scans;
morphing the virtual representation of the generic unresected contour of the hard tissue of interest in the virtual patient model into conformity with the unresected contour of the hard tissue of interest detected in the initial sequence of optical scans; and
morphing the virtual representation of the generic resected contour of the hard tissue of interest in the virtual patient model into conformity with the virtual representation of the generic unresected contour of the hard tissue of interest in the virtual patient model.

6. The method of claim 2, wherein accessing the virtual patient model comprises:
accessing the virtual patient model comprising a virtual representation of the unresected contour of the hard tissue of interest;
during the initial period of time, receiving a command from the surgeon specifying a set of target resection parameters for the hard tissue of interest; and
projecting the set of target resection parameters onto the virtual representation of the unresected contour of the hard tissue of interest to define the target resected contour of the hard tissue of interest; and
storing the target resected contour of the hard tissue of interest in the virtual patient model.

7. The method of claim 1:
further comprising, prior to the surgical operation:
accessing a pre-operative scan of the hard tissue of interest of the patient;
extracting a virtual representation of the unresected contour of the hard tissue of interest from the pre-operative scan;
generating a virtual representation of the target resected contour of the hard tissue of interest based on the virtual unresected contour of the hard tissue of interest and a pre-operative surgical plan defined by the surgeon;
compiling the virtual representation of the unresected contour of the hard tissue of interest and the virtual representation of the target resected contour of the hard tissue of interest into the virtual patient model; and
storing the virtual patient model, in association with the patient, in a database; and
wherein accessing the virtual patient model comprises, during the surgical operation, accessing the virtual patient model from the database.

8. The method of claim 1, further comprising:
during the first period of time:
prompting the surgeon to confirm intent of the spatial difference; and
in response to confirmation of intent of the spatial difference from the surgeon, prompting the surgeon to provide a reason for the spatial difference; and
in response to receipt of the reason from the surgeon, recording the spatial difference, confirmation of intent of the spatial difference, and the reason in the database and in association with the surgical operation.

9. The method of claim 1, further comprising:
detecting insufficient material removal from the hard tissue of interest based on the spatial difference;
in response to detecting insufficient material removal from the hard tissue of interest, serving a prompt to the surgeon to remove additional material from the hard tissue of interest;
during a second period of time succeeding a second resection of the hard tissue of interest within the surgical operation:
accessing a second sequence of optical scans recorded by the optical sensor;
detecting the set of features representing the patient in the second sequence of optical scans;
registering the virtual patient model to the hard tissue of interest in the surgical field based on the set of features; and
detecting a second actual resected contour of the hard tissue of interest in the second sequence of optical scans;
calculating a second spatial difference between the second actual resected contour of the hard tissue of interest detected in the second sequence of optical scans and the target resected contour of the hard tissue of interest represented in the virtual patient model registered to the hard tissue of interest in the surgical field; and
presenting the second spatial difference to the surgeon.

10. The method of claim 1:
wherein accessing the virtual patient model comprises accessing the virtual patient model defining the target resected contour of the hard tissue of interest and defining a second target resected contour of a second hard tissue of interest adjacent the hard tissue of interest;
further comprising:
detecting excessive material removal from the hard tissue of interest based on the spatial difference;
in response to detecting excessive material removal from the hard tissue of interest, modifying the second target resected contour of a second hard tissue of interest to compensate for excessive material removal from the hard tissue of interest.

11. The method of claim 10:
wherein accessing the virtual patient model comprises accessing the virtual patient model defining the target resected contour of the hard tissue of interest comprising a femur and defining a second target resected contour of a second hard tissue of interest comprising a tibia;
wherein calculating the spatial difference comprises detecting a spatial difference between actual resection of a femoral condyle of the patient and target resection of the femoral condyle of the patient;
wherein detecting excessive material removal from the hard tissue of interest comprises detecting resection of excessive material from the femoral condyle of the patient; and
wherein modifying the second target resected contour of the second hard tissue of interest to compensate for excessive material removal from the hard tissue of interest comprises reducing magnitude of resection of a tibial plateau of the patient to compensate for excessive material removal from the femoral condyle of the patient.

12. The method of claim 1:
wherein storing the spatial difference in the database with the corpus of spatial differences labeled with patient outcomes for the set of instances of the surgical operation within the population of patients comprises aggregating the corpus of spatial differences labeled with patient outcomes for the set of instances of the surgical operation performed by the surgeon;
wherein deriving the correlation between outcomes and spatial differences comprises deriving the correlation between:
    successful recoveries within the population of patients operated on by the surgeon; and
    spatial differences between actual resected contours of the hard tissue of interest and target resected contours of the hard tissue of interest specified in surgical plans defined by the surgeon; and
further comprising, for a second surgical plan defined by the surgeon for a second instance of the surgical operation planned for a second patient, serving a recommendation for adjustment of the second surgical plan, based on the correlation, to the surgeon prior to the second instance of the surgical operation.

13. The method of claim 1, further comprising, during the first period of time:
selecting a frame in the first sequence of optical scans;
projecting a virtual representation of an unresected contour of the hard tissue of interest, defined in the virtual patient model, onto the frame;
writing the spatial difference to the frame; and
serving the frame to a physician portal affiliated with a second surgeon located remotely from the surgical field.

14. The method of claim 1:
wherein accessing the virtual patient model comprises accessing the virtual patient model defining the target resected contour of a femoral condyle of a femur of the patient;
wherein detecting the actual resected contour of the hard tissue of interest in the first sequence of optical scans comprises detecting the actual resected contour the femoral condyle of the patient in the first sequence of optical scans; and
wherein detecting the spatial difference comprises detecting the spatial difference between the actual resected contour of the femoral condyle detected in the first sequence of optical scans and the target resected contour of the femoral condyle defined in the virtual patient model.

15. The method of claim 14:
wherein calculating the spatial difference comprises:
    calculating a distance magnitude difference between the actual resected contour of the femoral condyle and the target resected contour of the femoral condyle;
    calculating an orientation difference between the actual resected contour of the femoral condyle and the target resected contour of the femoral condyle; and
    characterizing a surface profile difference between the actual resected contour of the femoral condyle and the target resected contour of the femoral condyle; and
wherein presenting the spatial difference to the surgeon during the surgical operation comprises rendering the distance magnitude difference, the orientation difference, and the surface profile difference on a display present near the surgical field.

16. The method of claim 15, wherein rendering the distance magnitude difference, the orientation difference, and the surface profile difference on the display comprises, during the second period of time:
detecting a position of an augmented reality headset, worn by a surgeon and comprising the display, proximal the surgical field;
estimating a perspective of the surgeon viewing the surgical field based on the position of the augmented reality headset;
generating an augmented reality frame comprising a projection of the target resected contour of the hard tissue of interest of the patient, defined in the virtual patient model, from the perspective of the surgeon;
inserting the distance magnitude difference, the orientation difference, and the surface profile difference into the augmented reality frame; and
at the augmented reality headset, rendering the augmented reality frame.

17. The method of claim 1, further comprising:
calculating an absolute spatial difference between the actual resected contour of the hard tissue of interest detected in the first sequence of optical scans and an unresected contour of the hard tissue of interest defined in the virtual patient model;
accessing a second correlation between outcomes and absolute spatial differences between actual resected contours of the hard tissue of interest and unresected contours of the hard tissue of interest within the population of patients subject to instances of the surgical operation;
predicting a probability of successful outcome of the patient based on the absolute spatial difference and the second correlation;
in response to the probability of successful outcome exceeding a threshold probability, prompting the surgeon to move to a next step of the surgical operation; and
in response to the probability of successful outcome falling below the threshold probability, prompting the surgeon to correct the actual resected contour of the hard tissue of interest of the patient to reduce the spatial difference.

18. A method for tracking and adapting to deviations from surgical plans comprising:
- accessing a virtual patient model defining a target position of an artificial implant on a tissue of interest;
- during a first period of time succeeding placement of the artificial implant on the tissue of interest within a surgical operation:
  - accessing a first sequence of optical scans recorded by an optical sensor facing a surgical field occupied by a patient;
  - detecting a set of features representing the patient in the first sequence of optical scans;
  - registering the virtual patient model to the tissue of interest in the surgical field based on the set of features; and
  - detecting an actual position of the artificial implant on the tissue of interest in the first sequence of optical scans;
- calculating a spatial difference between the actual position of the artificial implant on the tissue of interest detected in the first sequence of optical scans and the target position of the artificial implant on the tissue of interest represented in the virtual patient model registered to the tissue of interest in the surgical field;
- presenting the spatial difference to a surgeon during the surgical operation;
- calculating an absolute position of the artificial implant on the tissue of interest detected in the first sequence of optical scans;
- accessing a correlation between outcomes and absolute positions of instances of the artificial implant on the tissue of interest within a population of patients subject to instances of the surgical operation;
- predicting a probability of successful outcome of the patient based on the absolute position of the artificial implant on the tissue of interest and the correlation;
- in response to the probability of successful outcome exceeding a threshold probability, prompting the surgeon to move to a next step of the surgical operation; and
- in response to the probability of successful outcome falling below the threshold probability, prompting the surgeon to adjust the absolute position of the artificial implant on the tissue of interest.

19. A method for tracking and adapting to deviations from surgical plans comprising:
- accessing a virtual patient model defining a target resected contour of a hard tissue of interest;
- during a first period of time succeeding resection of the hard tissue of interest within a surgical operation:
  - accessing a first sequence of optical scans recorded by an optical sensor facing a surgical field occupied by a patient;
  - detecting a set of features representing the patient in the first sequence of optical scans;
  - registering the virtual patient model to the hard tissue of interest in the surgical field based on the set of features; and
  - detecting an actual resected contour of the hard tissue of interest in the first sequence of optical scans;
- calculating a spatial difference between the actual resected contour of the hard tissue of interest detected in the first sequence of optical scans and the target resected contour of the hard tissue of interest represented in the virtual patient model registered to the hard tissue of interest in the surgical field;
- presenting the spatial difference to a surgeon during the surgical operation;
- calculating an absolute spatial difference between the actual resected contour of the hard tissue of interest detected in the first sequence of optical scans and an unresected contour of the hard tissue of interest defined in the virtual patient model;
- accessing a correlation between outcomes and absolute spatial differences between actual resected contours of the hard tissue of interest and unresected contours of the hard tissue of interest within a population of patients subject to instances of the surgical operation;
- predicting a probability of successful outcome of the patient based on the absolute spatial difference and the correlation;
- in response to the probability of successful outcome exceeding a threshold probability, prompting the surgeon to move to a next step of the surgical operation; and
- in response to the probability of successful outcome falling below the threshold probability, prompting the surgeon to correct the actual resected contour of the hard tissue of interest of the patient to reduce the spatial difference.

20. A method for tracking and adapting to deviations from surgical plans comprising:
- accessing a virtual patient model defining a target resected contour of a hard tissue of interest;
- further comprising, during an initial period of time preceding the first period of time and succeeding incision of the patient proximal the hard tissue of interest:
  - accessing an initial sequence of optical scans recorded by the optical sensor; and
  - detecting an unresected contour of the hard tissue of interest in the initial sequence of optical scans;
- during a first period of time succeeding resection of the hard tissue of interest within a surgical operation:
  - accessing a first sequence of optical scans recorded by an optical sensor facing a surgical field occupied by a patient; and
  - detecting an actual resected contour of the hard tissue of interest in the first sequence of optical scans;
- calculating an absolute spatial difference between the actual resected contour of the hard tissue of interest detected in the first sequence of optical scans and the unresected contour of the hard tissue of interest;
- presenting the absolute spatial difference to a surgeon during the surgical operation;
- labeling the absolute spatial difference with a post-operative outcome of the patient;
- storing the absolute spatial difference in a database with a corpus of absolute spatial differences labeled with patient outcomes for a set of instances of the surgical operation within a population of patients; and
- deriving a correlation between outcomes and absolute spatial differences between actual resected contours of the hard tissue of interest and unresected contours of the hard tissue of interest within the population of patients.

* * * * *